United States Patent [19]

Mast, Jr.

[11] 4,067,087
[45] Jan. 10, 1978

[54] METHOD OF FORMING TAMPONS AND ASSEMBLING SAME IN INSERTERS

[75] Inventor: John George Mast, Jr., Cincinnati, Ohio

[73] Assignee: The Procter & Gamble Company, Cincinnati, Ohio

[21] Appl. No.: 698,120

[22] Filed: June 21, 1976

Related U.S. Application Data

[62] Division of Ser. No. 531,222, Dec. 10, 1974, Pat. No. 4,006,515.

[51] Int. Cl.² .............................................. A61L 15/00
[52] U.S. Cl. ..................................................... 28/118
[58] Field of Search ................ 19/144.5, 149; 128/270, 128/285

[56] References Cited

U.S. PATENT DOCUMENTS

| | | | |
|---|---|---|---|
| 2,458,685 | 1/1949 | Crockford | 19/144.5 |
| 2,690,598 | 10/1954 | Bletzinger et al. | 19/144.5 |
| 3,875,615 | 4/1975 | Muckenfuhs | 19/144.5 |

*Primary Examiner*—Dorsey Newton
*Attorney, Agent, or Firm*—Melville, Strasser, Foster & Hoffman

[57] ABSTRACT

Procedures for continuously forming rosette shaped tampons from aggregate containing tubular sacks or overwraps having withdrawal strings at one end and assembling the tampons in inserters, rotary transfer mechanism being provided for engaging the withdrawal strings of the sacks and sequentially delivering them to a rotary assembly turret having a multiplicity of assembling stations mounted around its periphery. Each inserter comprises inner and outer parts, and feeding means are provided to individually feed and position an inner inserter and an outer inserter in holders at each assembly station. Each station has a reciprocating string engaging rod which acts to remove a sack by its string from the transfer mechanism and positions the sack to be drawn upwardly by vacuum into an overlying annular inversion chamber wherein the sack is inverted into rosette shape by the action of a pressure-vacuum reciprocating inversion rod. The shaped sack is then moved downwardly into an underlying compression cone wherein it is radially compressed and drawn downwardly into an underlying cylindrical compression chamber, whereupon the outer inserter is positioned to overlie the compression chamber and the inner inserter, which underlies the compression chamber, is moved upwardly by a reciprocating assembly rod which causes the inner inserter to push the compacted tampon upwardly into the overlying outer inserter, and at the same time the upper end of the inner inserter engages within the outer inserter to complete the assembly. The assembled inserter is then transferred from the assembly station to a discharge wheel for delivery to a collection station or other mechanism for wrapping, packaging, or the like as the rotary assembly turret completes its cycle of operation.

11 Claims, 46 Drawing Figures

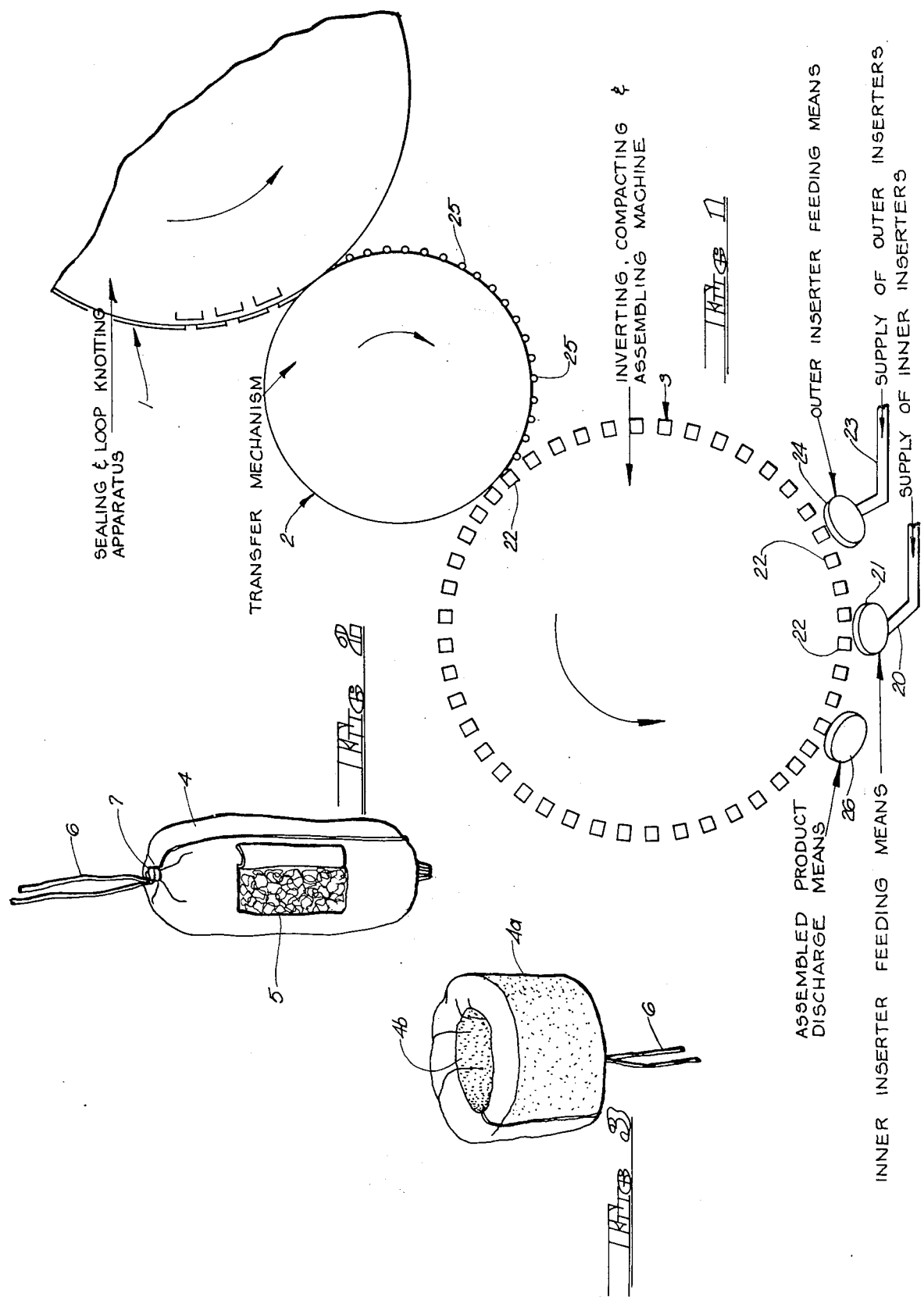

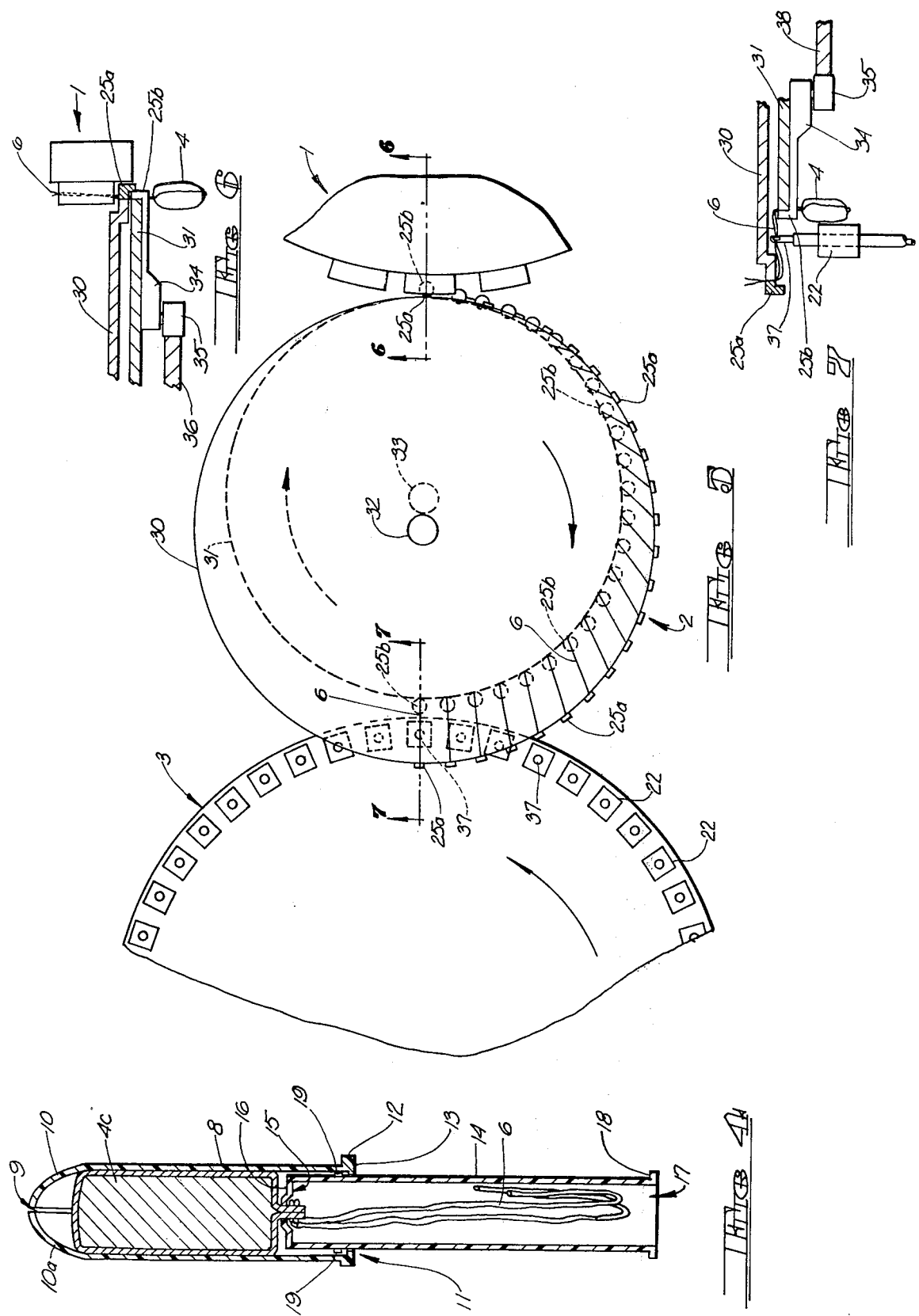

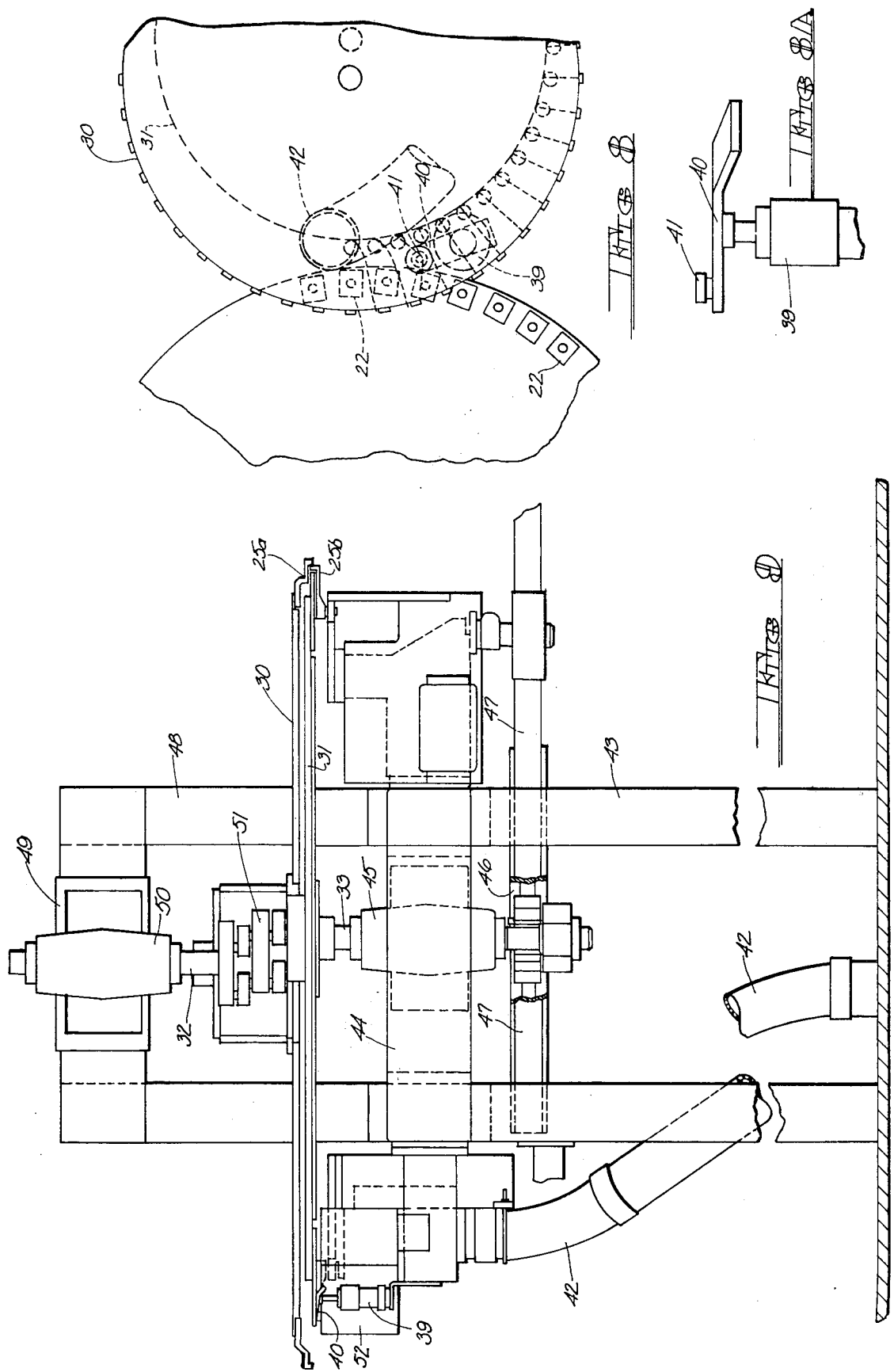

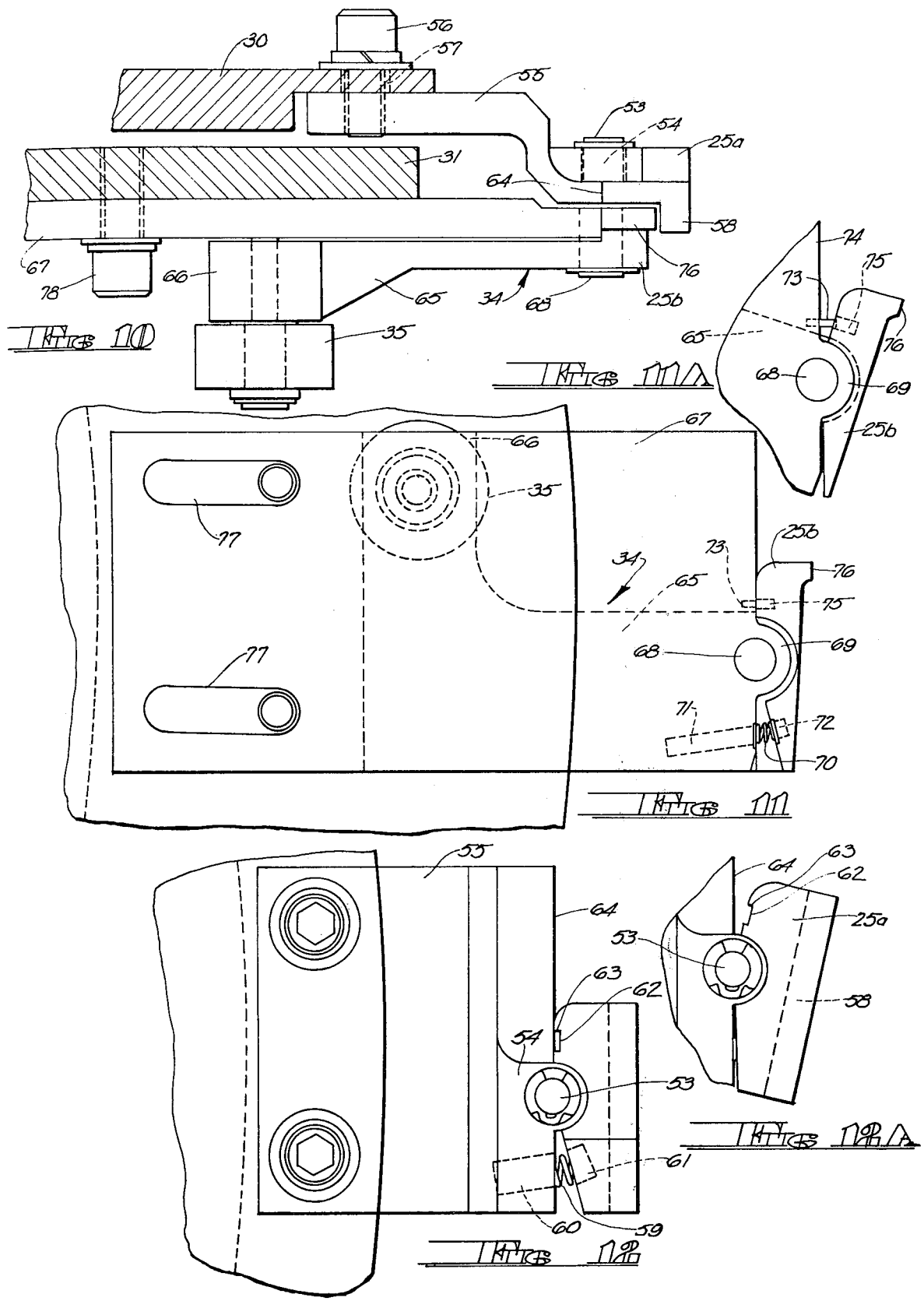

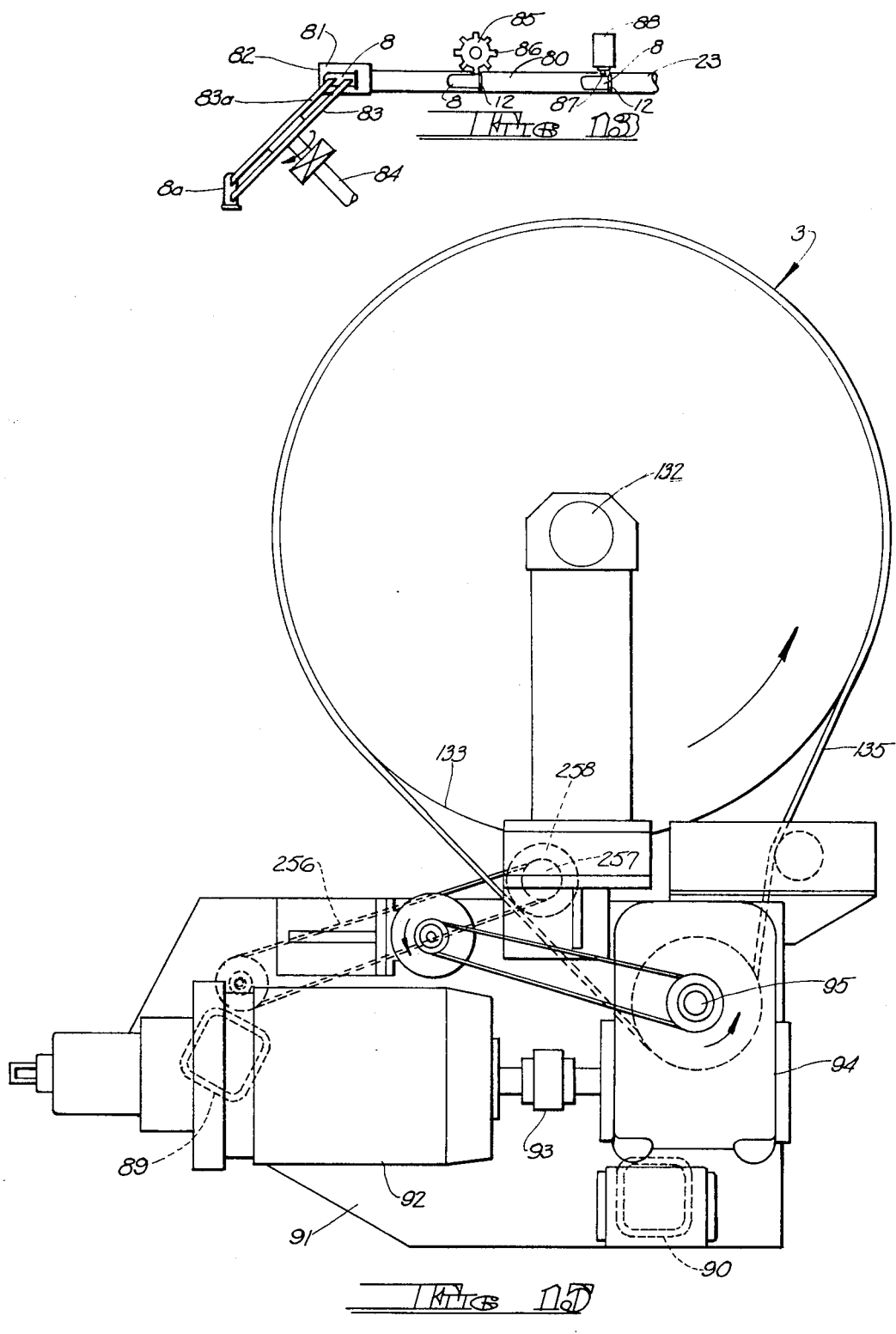

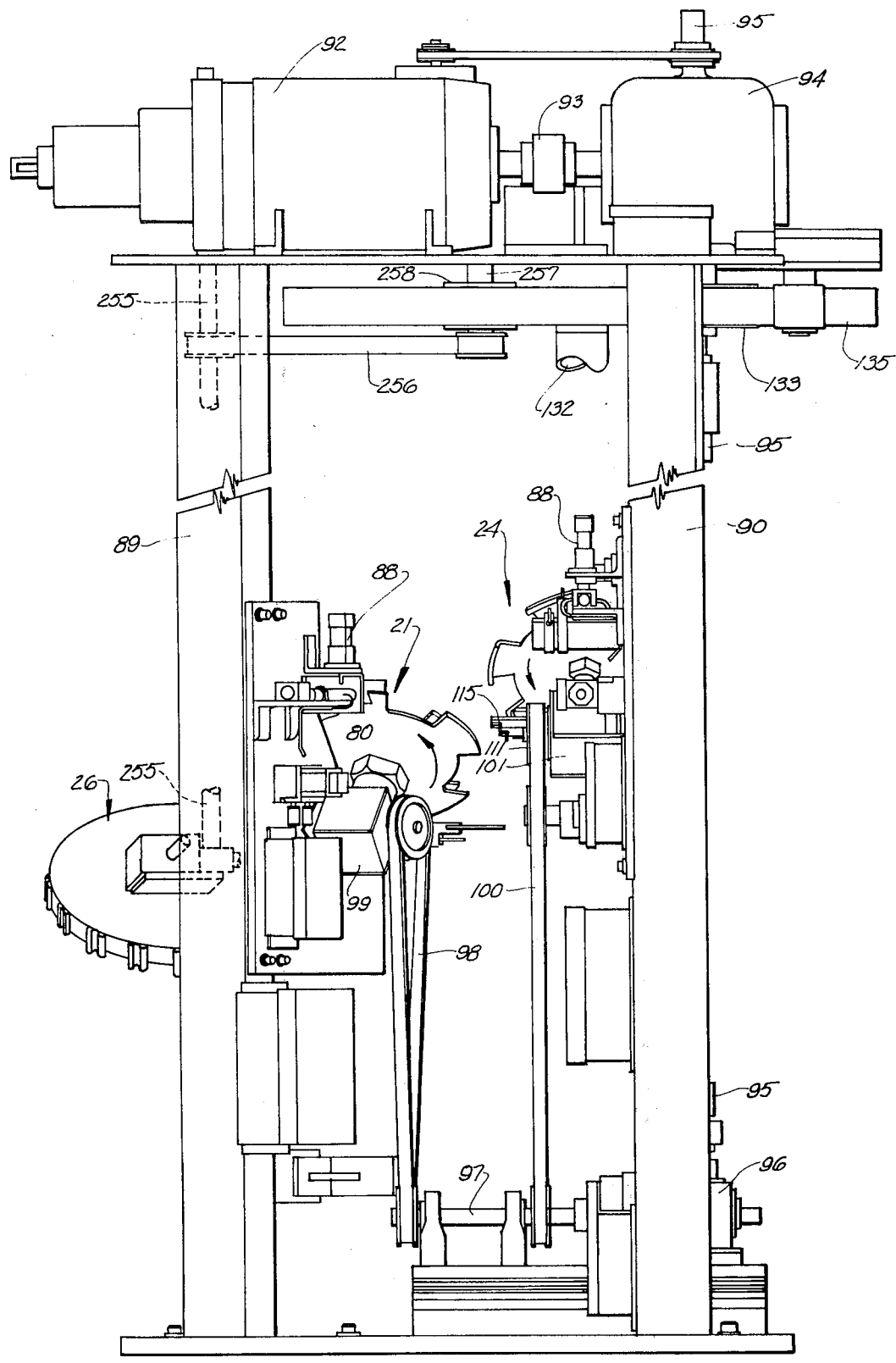

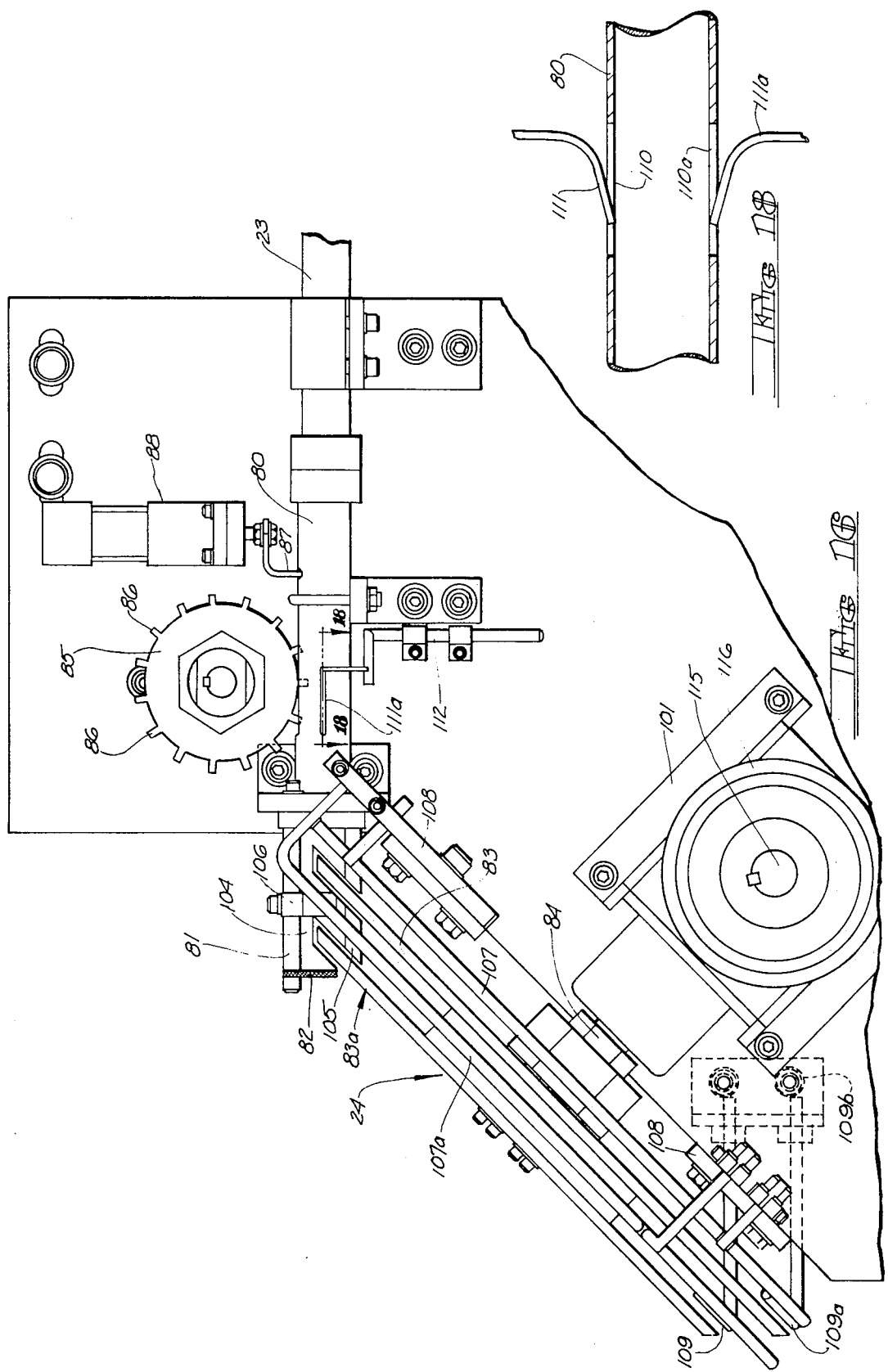

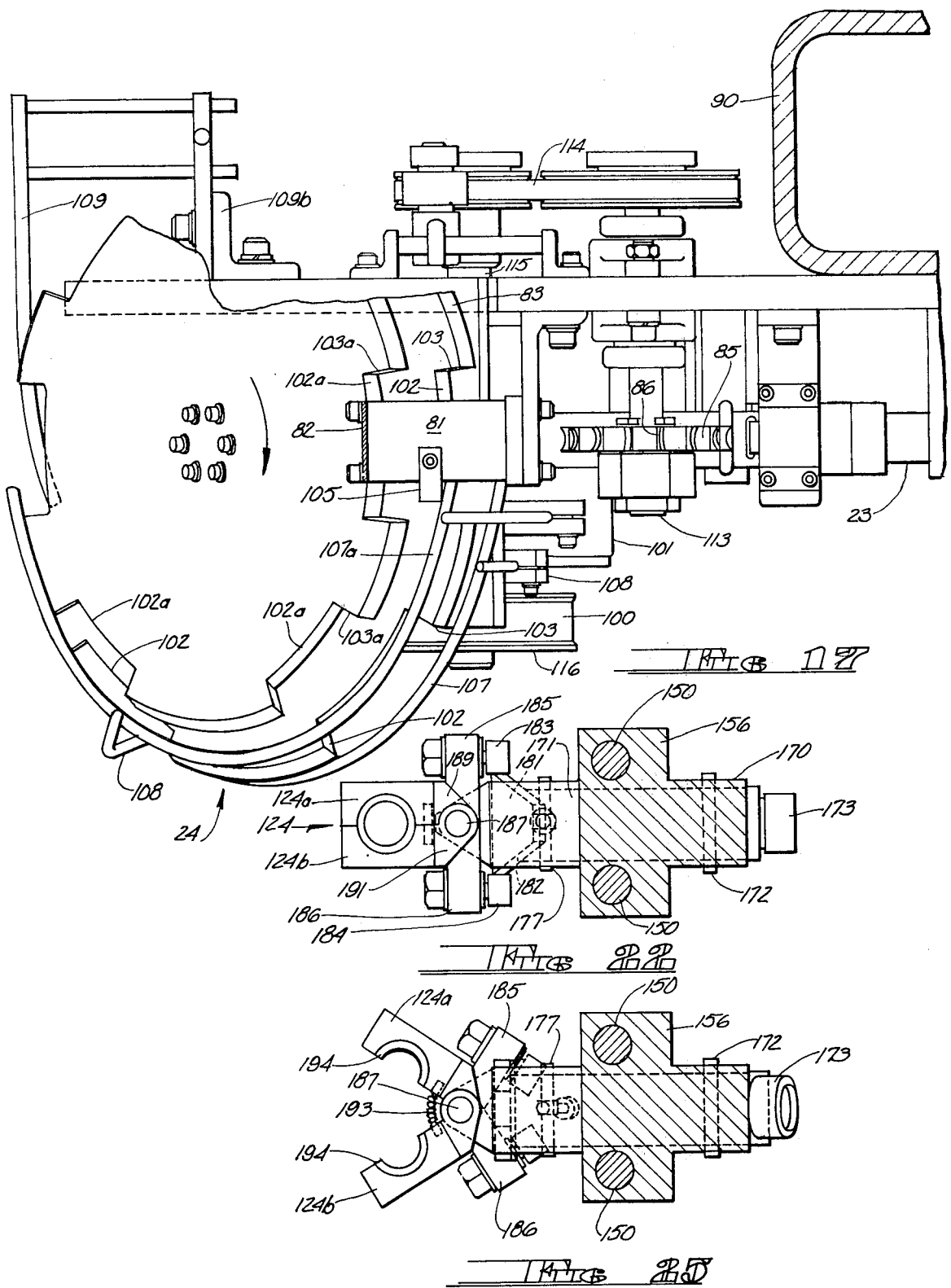

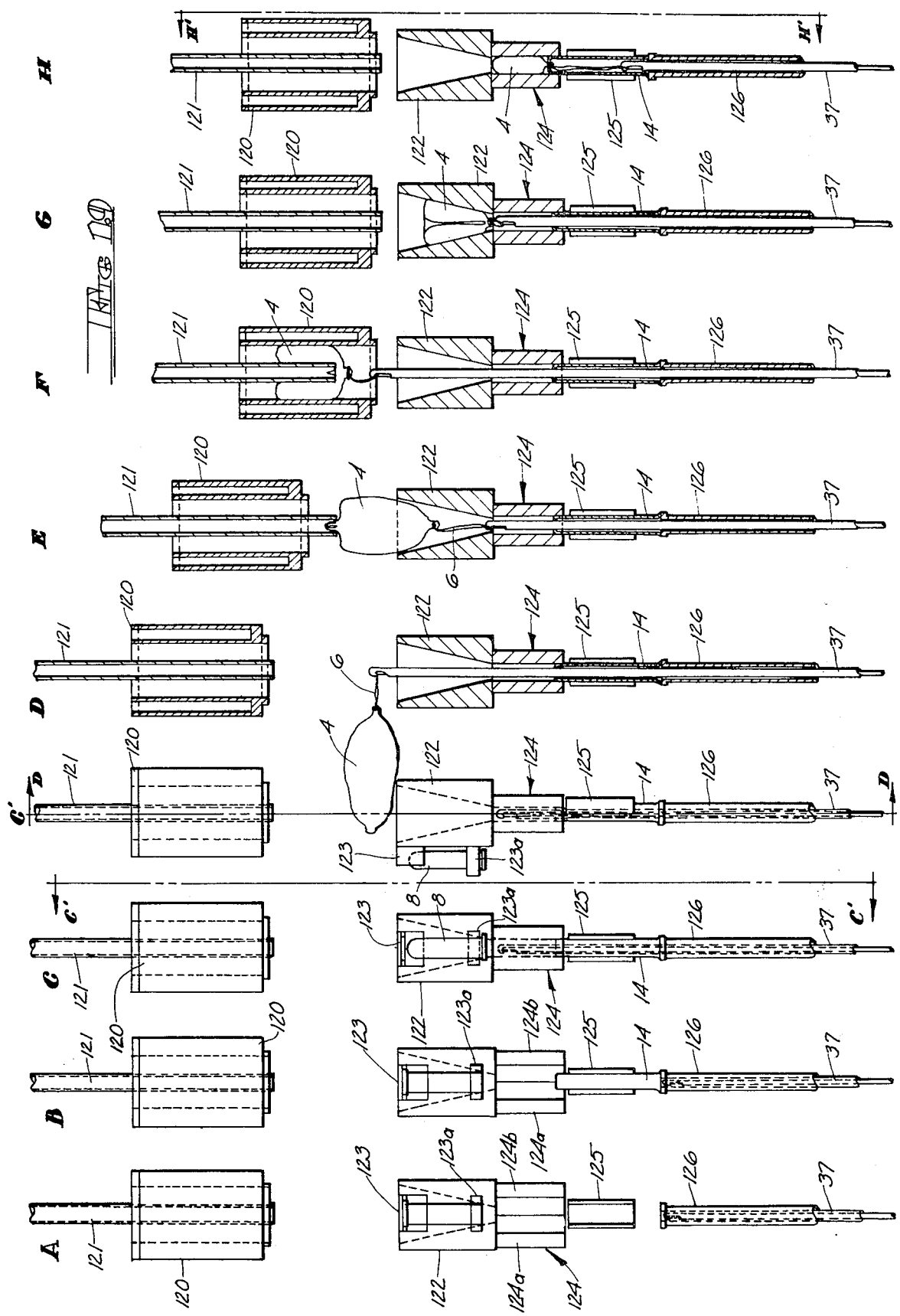

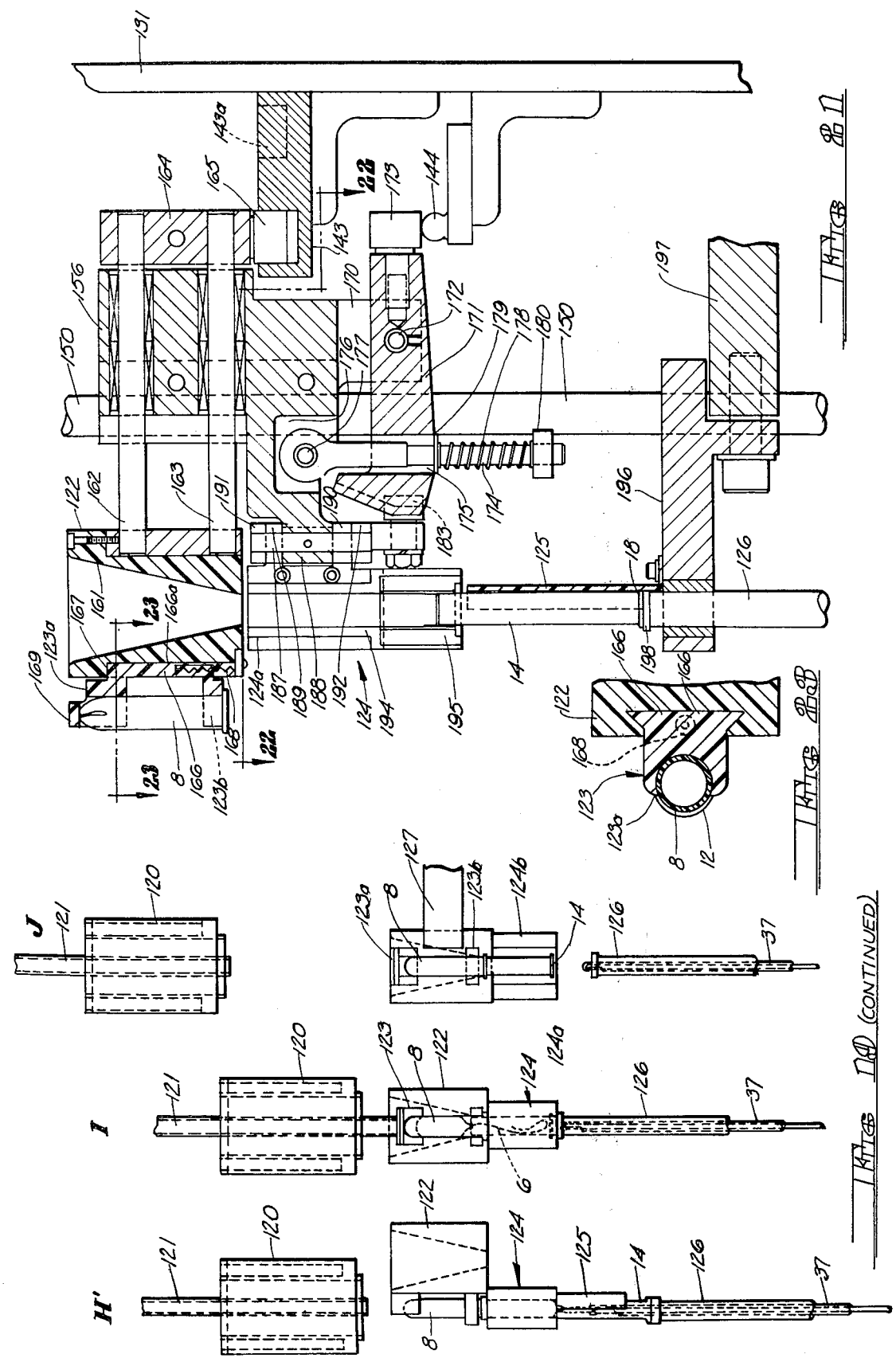

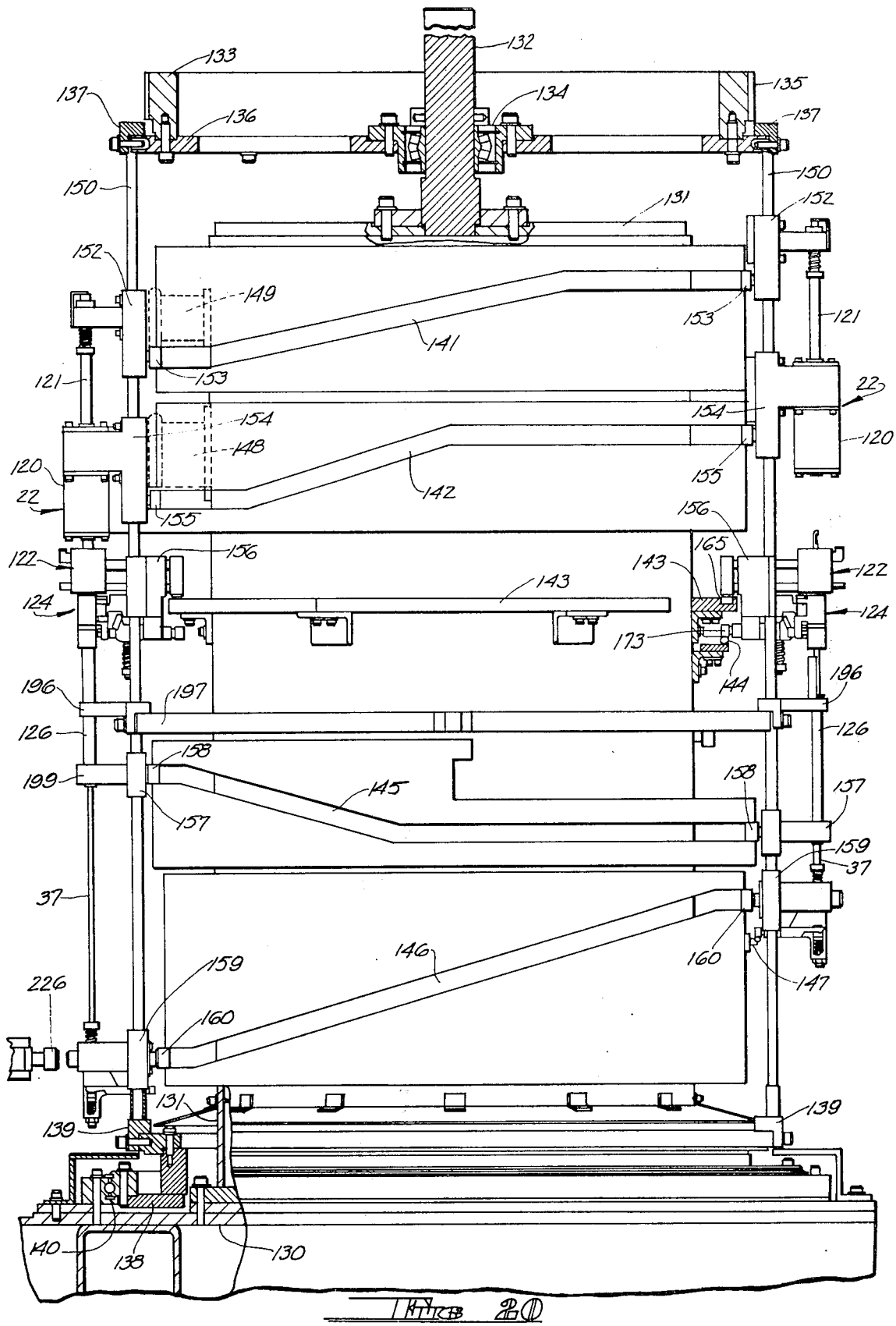

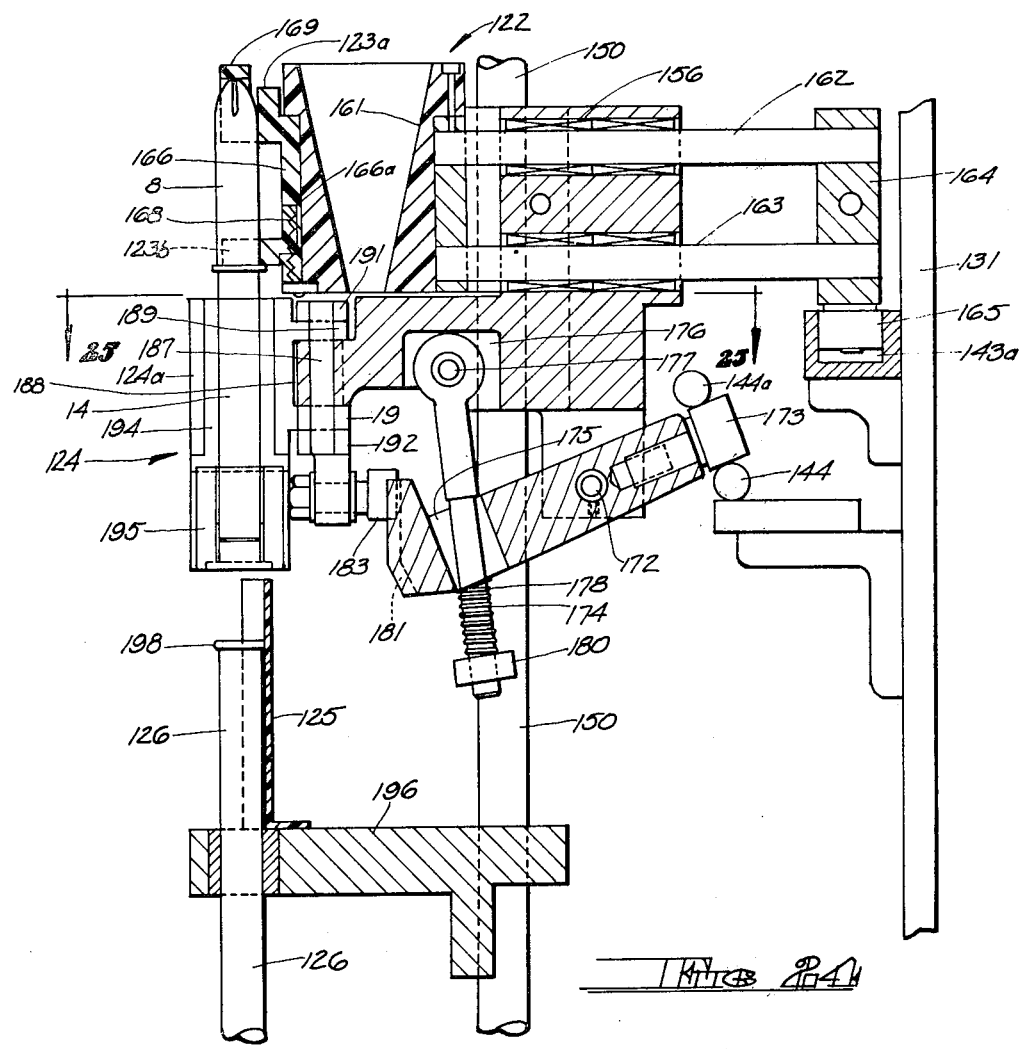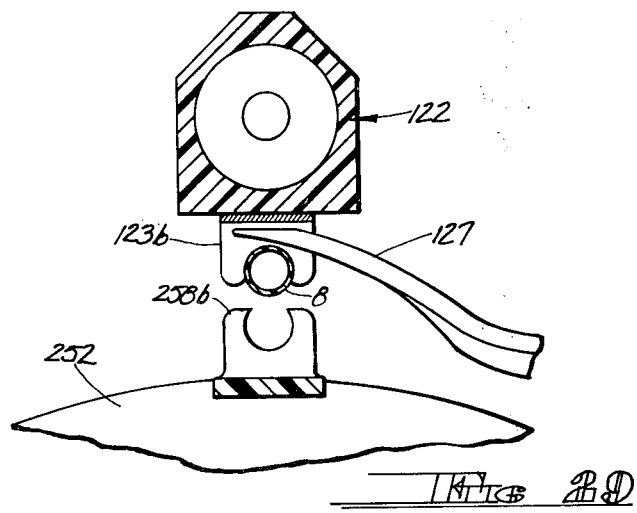

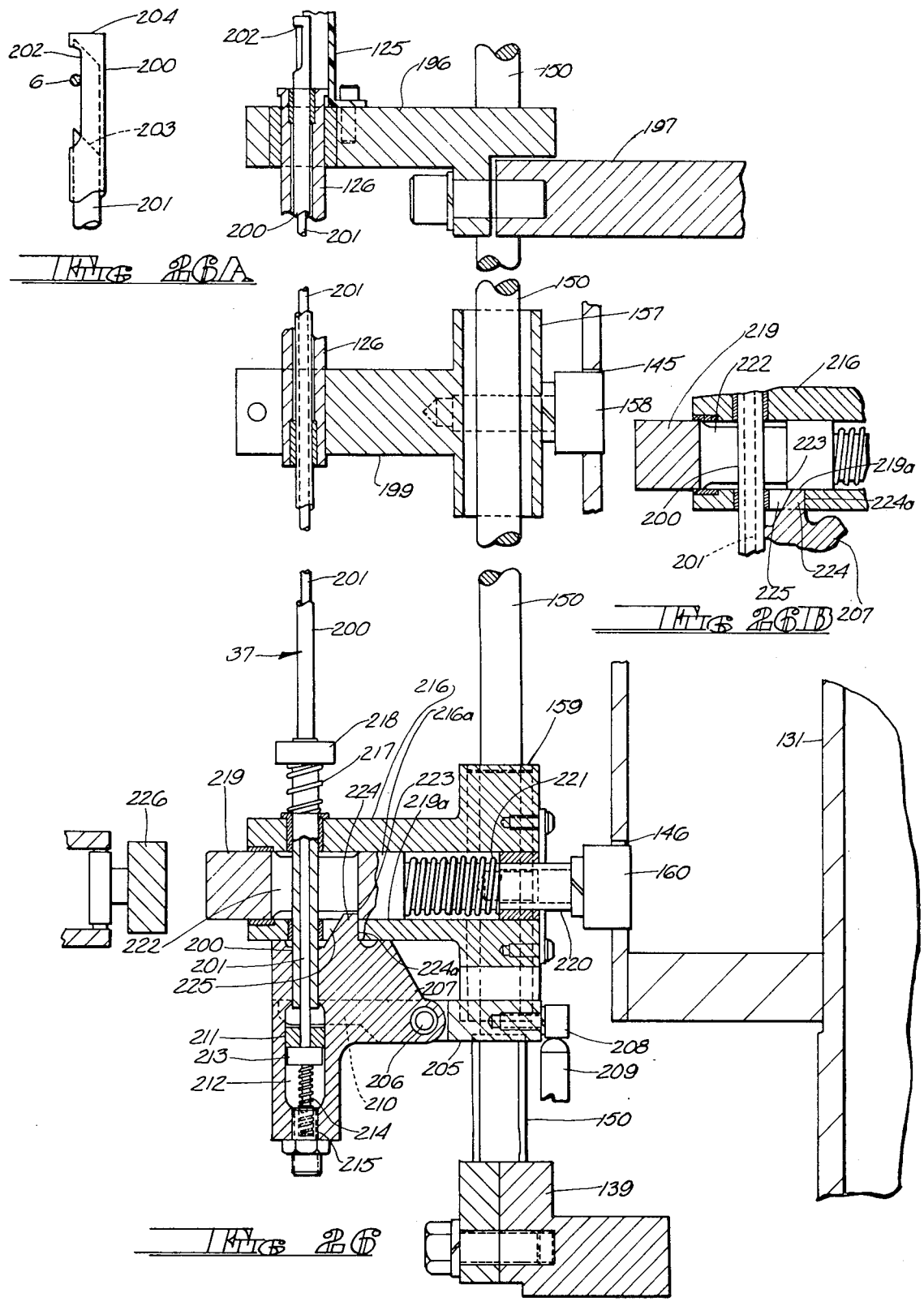

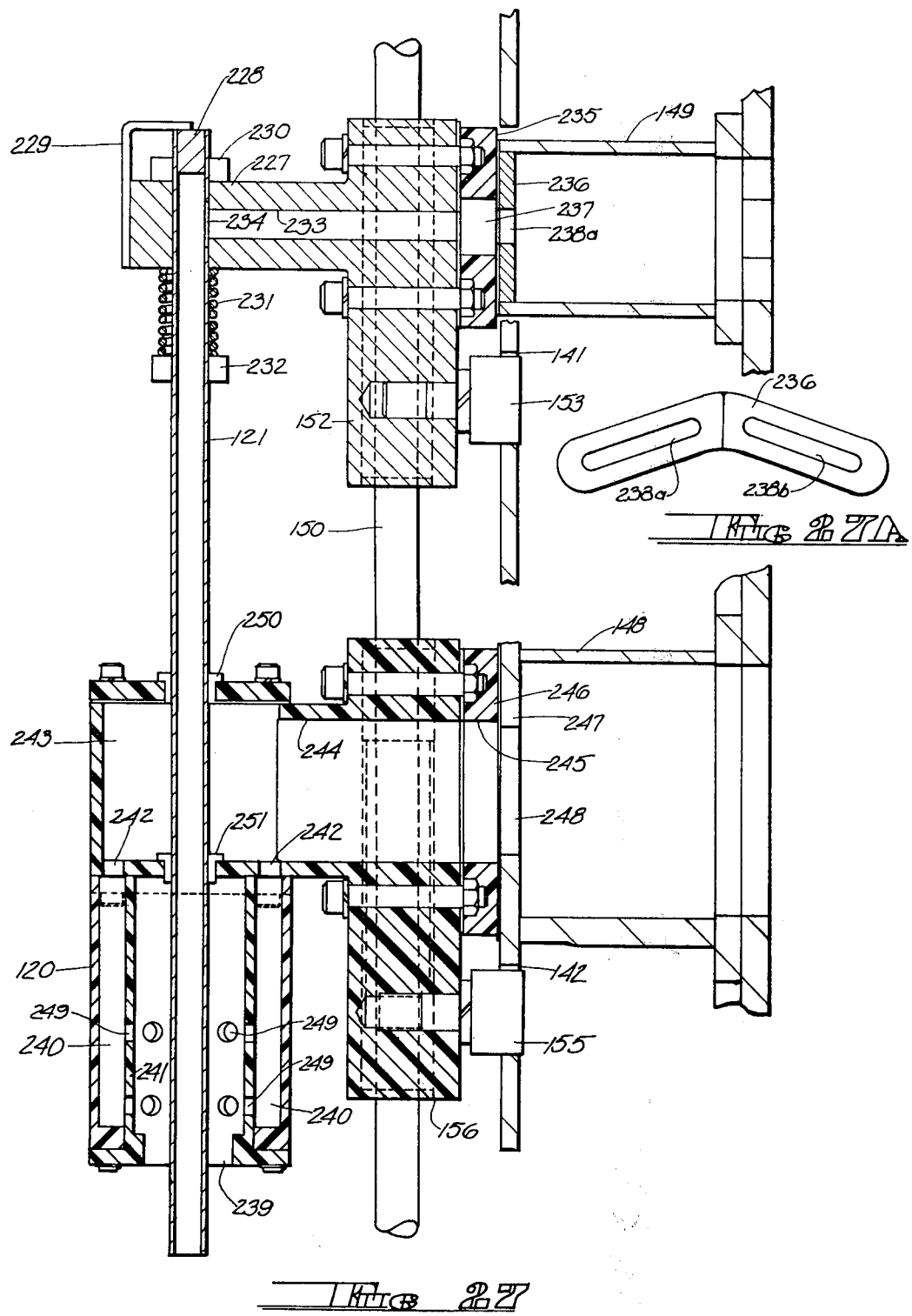

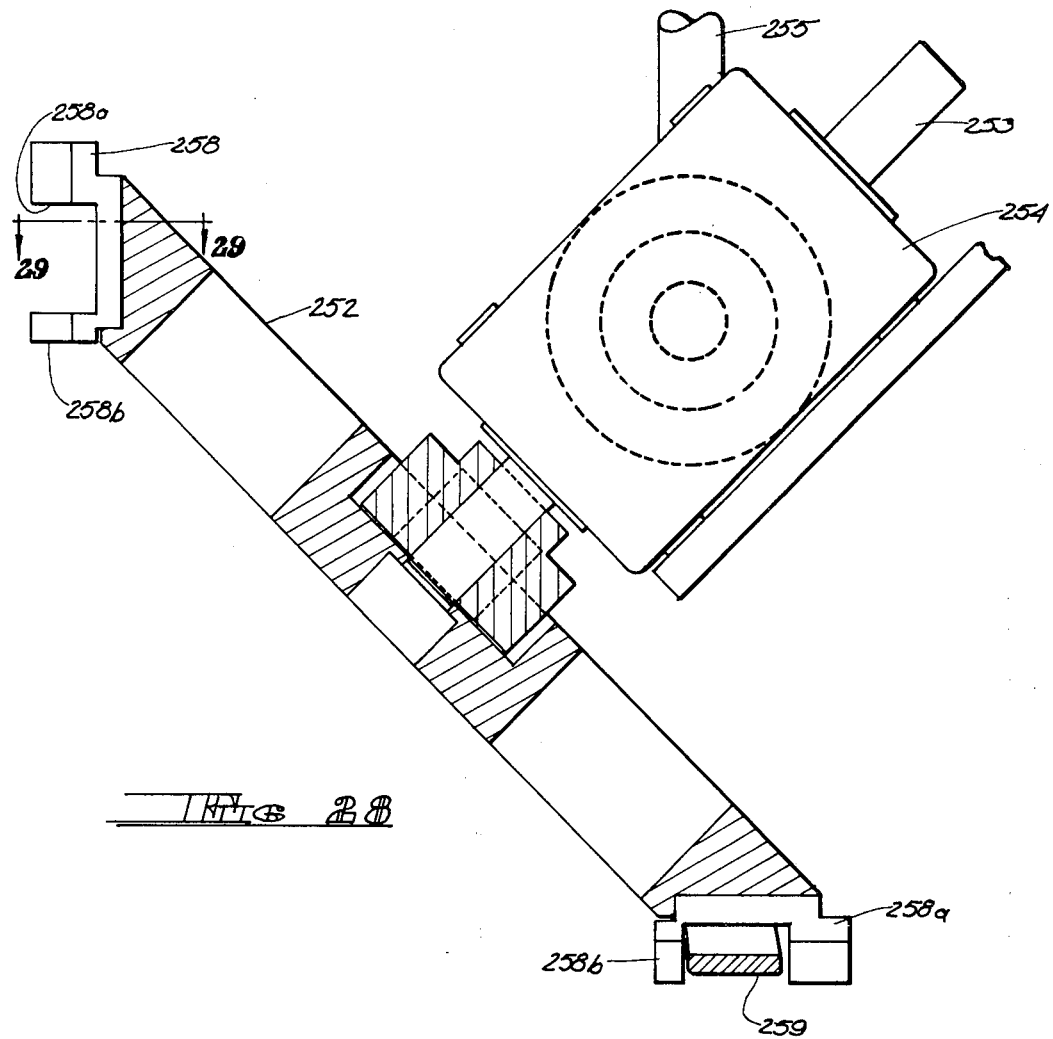

METHOD OF FORMING TAMPONS AND ASSEMBLING SAME IN INSERTERS

This is a division of application Ser. No. 531,222, filed Dec 10, 1974 now U.S. Pat. No. 4,006,515.

BACKGROUND OF THE INVENTION

1. The Field of Invention.

The present invention has to do with the manufacture of tampons and more specifically with the continuous formation of rosette shaped tampons from aggregate containing tubular sacks or overwraps having a withdrawal string at one end, followed by the assembly of the tampons with a two-piece tube-type inserter by means of which the tampon may be inserted into a vagina.

2. Description of the Prior Art.

Tampons of the type to which this invention relates are disclosed in commonly owned U.S. Pat. No. 3,815,601, dated June 11, 1974, and entitled "Catamenial Aggregate Absorbent Body." In accordance with the teachings of the said patent, the tampon comprises aggregate composed of individual pieces of absorbent, foam-like material encased within a flexible, fluid-permeable overwrap in the form of a tubular sack closed at its opposite ends, the ends of the sack preferably being gathered inwardly and secured to form end seals. A withdrawal string is attached to one end of the sack, which is preferably elongated, and the sack is inverted to form it into rosette shape by displacing inwardly the distal end of the sack, i.e., the end of the sack opposite the withdrawal string is displaced inwardly to form a cavity in the overwrap, thereby forming a tampon structure in which the absorbent aggregate is encased by an overwrap having an exterior portion forming the exterior surface of the tampon and a re-entrant portion forming the surface of the cavity. Following formation of the tampon into rosette shape, it is radially compressed and enclosed in a tube-type inserter having a head or outer part in which the the tampon is contained and an inner or plunger part by means of which the tampon is expelled from the inserter.

Mechanism and procedures for forming and filling tampon sacks of the character described are disclosed in commonly owned United States Application Ser. No. 484,813, in the name of Jean E. Schaefer, filed July 1, 1974 and entitled "Apparatus And Method For Continuously Forming And Filling Tampon Sacks," now U.S. Pat. No. 3,982,374, issued Sept. 28, 1976. In accordance with the teachings of this application, a web of sack forming material is printed with adhesive at spaced apart intervals at which end seals for the sacks are to be formed, the adhesive dried, and the web tubed around a hollow mandrel with the longitudinal edges of the web overlapped and sealed to form the longitudinal seam of the tubing. The tubing is fed to a rotating turret having a plurality of pleating and sealing stations which sequentially engage and gather the tubing and seal it together in the areas of the previously applied adhesive to form a continuous series of sacks. As the leading end seal of each successive sack is formed, a charge of aggregate is introduced into the tubing through the mandrel around which it is formed and propelled through the tubing so that the material comes to rest against the leading end seal of the sack being formed, whereupon the formation of the next successive end seal completes the sack and encloses the deposited charge of material. The sacks so-formed may then be provided with withdrawal strings which are stitched or tied to one of the end seals and the sacks cut apart to form individual units.

In another form of apparatus disclosed in commonly owned U.S. application Ser. No. 517,110 by Ronald W. Kock, filed Oct. 22, 1974 and entitled "Loop Knot Tying Method And Apparatus", now U.S. Pat. No. 3,940,169, issued Feb. 24, 1976, the tampon sacks may be fabricated on a rotating device carrying a plurality of operating heads which, in addition to pleating and sealing the web at spaced apart intervals to form sacks, is provided with means for attaching withdrawal string, including means for metering the correct length of string, cutting the string, piercing the sack in the area of an end seal, forming a loop knot through the pierced hole in the end seal, and severing the sacks intermediate the end seals to provide individual tampon sacks suspended by their withdrawal strings for discharge from the device.

The transfer mechanism of the present invention is specifically designed to engage the strings of tampon sacks fabricated on the apparatus just described and transfer them to the assembly turret for conversion into finished products.

Reference is also made to commonly owned co-pending application Ser. No. 400,620, by Delmar R. Muckenfuhs, filed Sept. 25, 1973, and entitled "Device And Method For Forming Tampon," now U.S. Pat. No. 3,875,615, issued Apr. 18, 1975, which teaches the formation of the closed tubular sacks into rosette shape. A cylindrical holding chamber is provided into which the tubular sack is inserted and expanded radially outwardly by a vacuum drawn on the holding chamber, a reciprocating tubular plunger sequentially acting to guide the sack into the holding chamber, displace the distal end of the sack inwardly to form it into rosette shape, and thereafter eject the shaped tampon from the holding chamber. Aspects of this invention are utilized in the present invention to effect formation of the sacks into rosette shape.

SUMMARY OF THE INVENTION

In accordance with the invention, an integrated system is provided for receiving the tampon sacks in filled and closed condition, with withdrawal string attached, orienting the string in predetermined position and presenting the string for engagement by the assembly turret which mounts a plurality of heads or stations each of which utilizes vacuum, low pressure air and a number of mechanical motions to invert the sack, compress the inverted sack and assemble it with an inserter having inner and outer parts, the system also including feeder units for delivering the inner and outer inserters to the assembly turret and positioning them at each station, together with a discharge mechanism for removing the completed product from the assembly turret.

The transfer mechanism for receiving and delivering the tampon sacks to the assembly turret comprises a transfer wheel having top and bottom discs each mounting about its periphery coacting sets of string gripping jaws which grasp the withdrawal string at two closely spaced apart points. The top and bottom discs of the transfer wheel are mounted on different centers and, as the wheel rotates, the upper and lower sets of gripping jaws in each set move toward and away from each other. The sets of gripping jaws are in vertical alignment when the withdrawal string is initially engaged, whereupon the jaws begin to move away from each other causing the string to be partially pulled through the looser top jaw so as to suspend the string substantially horizontally between the jaws as they approach the assembly turret. The horizontally disposed string runs into a vertical string grabber rod on the assembly turret which opens just prior to the string reaching it, and snaps shut as soon as the string is in its clamping jaw, whereupon the lower gripping jaw opens to release the string and the assembly turret pulls the string from the open lower gripping jaw and out of the closed upper jaw. The transfer mechanism also incorporates means for rejecting unwanted tampon sacks comprising a reject pin movable into the path of the horizontally disposed string just before transfer to the assembly turret. The reject pin engages the string and pulls it out of the upper gripper jaw resulting in the bag being held only by the lower gripping jaw, which makes transfer to the assembly turret impossible. When the lower gripping jaw opens after transfer should have taken place, the rejected sack falls into a reject chute.

The assembly turret consists of three main parts, a support structure, a series of cams, and a series of operating stations or heads. The support structure is the skeleton of the machine and supports the cams and stations. The cams move the various operating components of each station according to the cam paths, thereby programming the stations to make the motions necessary to form and assemble the product. The cams are internal with respect to the stations, thereby providing for easy removal of the stations and good machine visibility. The stations are mounted on vertical axes around the outside surface of the turret and revolve around the cams, making one complete tampon during each revolution or operating cycle of the turret.

The inner and outer inserters are separately fed to the assembly turret by feeder wheels which are of essentially identical construction, the inserter parts being fed to their respective feeder wheels by air flowing through conveyor tubes which deliver the inserter parts horizontally in nose to tail relation. The parts are separated from the conveying air flow by a screen which readily passes the air but stops the nose of the conveyed part in proper position for transfer by the feeder wheel. Upon engagement by the feeder wheel, the inserter is accelerated sideways and turned through an angle of 90° to bring it up to a surface speed and position matching a station on the assembly turret, whereupon it is pushed into a holder by rails or sweeps when the part is in vertical alignment with a station on the turret. In the case of the feeder for the outer inserters, it is preferred to provide an escapement wheel to hold the second inserter back while the first is being engaged and moved sideways by the feeder wheel to prevent damage to the nose portions of the outer inserters which have resilient petals which deflect outwardly as the tampon is ejected. Since the noses of the inner inserters are relatively flat and do not have fragile petals, an escapement wheel is not required for the inner inserters. Each feeder is also provided with high pressure air jets to speed up the movement of the inserters into the feeder wheel, and gate means are provided to prevent the feeding of inserters when they are not needed.

Each of the heads of stations on the assembly turret performs a plurality of operations during each revolution of the assembly turret. These operations are essentially as follows:

1. Inner Inserter Feed — Since the feeder wheel brings the inserters up to matched speed and pitch with the turret, fixed rails are used to push the inserters sideways out of the feeder wheel into vertically disposed holders on the turret. String grabber rods then commence upward movement through the axes of the inner inserters to hold them in place.

2. Outer Inserter Feed — This is similar to the inner inserter feed except that the outer inserters snap into holders which engage and grip the outside diameter of the outer inserters, each holder being mounted on the outer surface of a compression cone forming a part of each station.

3. Sack Transfer — When each station is roughly one-quarter of the way around the assembly turret from where the inserters are engaged, it is ready to receive a tampon sack delivered to the turret by the transfer wheel. The transfer wheel presents the withdrawal string horizontally in alignment with the upper end of the string grabber rod which has now moved upwardly through the compression cone which is in axial alignment with the inner inserter and the grabber rod. The surface speed of the transfer wheel is slightly greater than the assembly turret and the string will overrun the grabber rod which snaps shut on the string, whereupon the grabber rod pulls the tampon sack free from the transfer wheel and begins to pull it into the compression cone as the grabber rod begins retracting movement.

4. Sack Alignment — In order to produce a uniformly inverted (rosette shape) product, the inversion process must commence with the sack in vertical position with its distal end uppermost. To accomplish this, the grabber rod pulls the sack into the compression cone by a distance sufficient to cause the longitudinal axis of the sack to be aligned with the longitudinal axis of the cone.

5. Inversion — An annular inversion chamber containing an axially aligned hollow inversion tube overlies the compression chamber and begins to move downwardly as the tampon sack is seated in the compression cone. By interaction of the hollow inversion tube which grasps the distal end of the sack by means of vacuum, and by vacuum drawn on the inversion chamber, the sack is drawn into the chamber and inverted over the inversion tube. To insure that the inversion is uniform, i.e., the re-entrant portion of the sack centered with respect to the exterior portion, the string slackness is controlled so that the sack cannot tilt on the inversion tube. Once the product is fully draped around the inversion tube, the vacuum drawn on both the inversion chamber and the inversion tube is terminated and the inversion tube moves downwardly, the inverted sack being blown off the inversion tube by air under pressure passing through the tube.

6. Compression — The inverted sack is compressed by pulling it downwardly by its string, the string grabber rod pulling the inverted stack through the funnel-shape compression cone and into an underlying cylindrical compression chamber through which the string grabber rod also passes. As the string grabber rod approaches its fully retracted position, the string is released at a point which leaves it in a tucked position inside the inner inserter which is positioned immediately beneath the compression chamber.

7. Inserter Assembly — In order to bring the outer inserter into alignment with the compressed tampon and the underlying inner inserter, the compression cone, which mounts the holder for the outer inserter, is shifted radially inwardly until the outer inserter overlies and is in axial alignment with the cylindrical compression chamber, whereupon the outer inserter holder is deflected downwardly by the overlying inverter tube to seat the enlarged lowermost end of the outer inserter on the upper surface of the inversion chamber. An assembly rod which surrounds the string gripper rod and underlies the lowermost end of the inner inserter is then moved upwardly, thereby forcing the compressed tampon and the inner inserter into the outer inserter. Preferably the lower portion of the compression chamber, which is longer than the inner inserter, is formed with a resilient cushioning material so that the enlarged lowermost end of the inner inserter may pass into the compression chamber without damage.

8. Discharge — The compression is made in two parts which may be pivoted to an open position so that the assembled product can be carried sideways out of the compression chamber by the outer inserter holder which is then displaced radially outwardly to present the assembled product to a sweep or stripper which displaces the product laterally from the outer holder into jaws on a discharge wheel which transfers it to a collection station, such as an infeed conveyor which conveys the product to a wrapping unit, a sweep or stripper being positioned to remove the product from the discharge wheel at a point remote from the assembly turret.

DESCRIPTION OF THE DRAWINGS

FIG. 1 is a diagrammatic plan view illustrating the general organization of apparatus in accordance with the invention.

FIG. 2 is a perspective view with parts broken away of a tampon sack prior to formation into rosette shape.

FIG. 3 is a perspective view showing the tampon sack after formation into rosette shape.

FIG. 4 is a vertical sectional view of the compacted tampon assembled in a two-piece tube type inserter.

FIG. 5 is a diagrammatic plan view illustrating the general operation of the transfer mechanism.

FIG. 6 is an enlarged vertical sectional view taken along the line 6—6 of FIG. 5.

FIG. 7 is an enlarged vertical sectional view taken along the line 7—7 of FIG. 5.

FIG. 8 is a fragmentary diagrammatic plan view illustrating the operation of reject means utilized in conjunction with the transfer mechanism.

FIG. 8A is an enlarged fragmentary perspective view of the reject means.

FIG. 9 is a side elevational view of the transfer mechanism broken away.

FIG. 10 is an enlarged side elevational view of a set of upper and lower gripping jaws for the transfer mechanism.

FIG. 11 is a plan view illustrating the details of the lower gripping jaw assembly, with the jaw in closed position.

FIG. 11A is a fragmentary plan view similar to FIG. 11 illustrating the lower gripping jaw in open position.

FIG. 12 is a plan view illustrating the details of the upper gripping jaw assembly, with the jaw in closed position.

FIG. 12A is a fragmentary plan view similar to FIG. 12 illustrating the upper gripping jaw in open position.

FIG. 13 is a diagrammatic side elevational view illustrating the operation of the inserter feeding means.

FIG. 14 is a side elevational view of the inserter feeding means and the drive means for the various components.

FIG. 15 is a top plan view of the drive means shown in FIG. 14.

FIG. 16 is an enlarged partial side elevational view of the outer inserter feeding means.

FIG. 17 is a plan view, with parts broken away, of the inserter feeding means shonw in FIG. 16.

FIG. 18 is an enlarged vertical sectional view taken along the line 18—18 of FIG. 16 illustrating the air jets for the inserter feeding means.

FIG. 19 is a diagrammatic side elevational view illustrating at A through J the successive positions assumed by each operating head during its cycle of operation, the positions C' and H' being the same as positions C and H, respectively, but taken at right angles thereto, and the positions D through H being sectional views taken along the line D—D of position C'.

FIG. 20 is a side elevational view with parts broken away of the assembly turret.

FIG. 21 is an enlarged vertical sectional view of the inversion cone, compression chamber and assembly tube portions of the operating head.

FIG. 22 is a sectional view taken along the line 22—22 of FIG. 21.

FIG. 23 is an enlarged sectional view taken along the line 23—23 of FIG. 21.

FIG. 24 is a vertical sectional view similar to FIG. 21 but showing the parts in an alternate position of use.

FIG. 25 is a sectional view taken along the line 25—25 of FIG. 24.

FIG. 26 is an enlarged vertical sectional view with parts broken away illustrating the assembly tube and string grabbing rod assembly.

FIG. 26A is an enlarged fragmentary elevational view of the uppermost end of the outer string grabber rod with the inner rod in retracted position.

FIG. 26B is a fragmentary sectional view similar to FIG. 26 illustrating the plunger in its alternate position.

FIG. 27 is an enlarged vertical sectional view illustrating the inversion tube and inversion chamber.

FIG. 27A is a reduced diagrammatic elevational view of the vacuum-pressure ports for the inverstion tube.

FIG. 28 is a side elevational view of the rotary discharge means with the discharge wheel shown in vertical section for clarity of illustration.

FIG. 29 is a sectional view taken along the line 29—29 of FIG. 28.

DESCRIPTION OF THE PREFERRED EMBODIMENTS

General Organization

For a general understanding of the organization and operation of the apparatus, reference is first made to FIG. 1 of the drawings wherein reference numeral 1 indicates mechanism by means of which tubular tampon sacks are suspended by their withdrawal strings and presented for transfer by the rotary transfer mechanism 2 to the rotary inverting, compacting and assembly machine 3, which will be referred to as the assembly turret. Preferably, the mechanism 1 will comprise sealing and loop knotting apparatus of the character described in the aforementioned commonly owned application Ser. No. 517,110, which fabricates the tampon sacks and attaches their withdrawal strings, the tampon sacks so-formed being suspended by their withdrawal strings for discharge from the device. It is to be understood, however, that the apparatus by means of which the tampon sacks are formed and their withdrawal strings attached, does not constitute a part of the present invention, but rather is merely indicative of apparatus which will present the suspended tampon sacks to the transfer mechanism 2 which forms a part of the present invention and comprises the means by which the tampon sacks are delivered in timed relation to the movement of the assembly turret 3.

A tampon sack of the type which will be delivered to transfer mechanism 2 is illustrated in FIG. 2, the structure comprising a tubular sack or overwrap 4 containing an aggregate 5 composed of individual pieces of absorbent foam-like material which is loosely encased within the overwrap. A withdrawal string 6 is securely attached to one end of the overwrap, as at the end closure 7. While in the embodiment illustrated the withdrawal string engages the end closure at approximately its mid-point and hence has two free end portions, it is deemed herein to comprise a single withdrawal string since it functions as a single string irrespective of whether it has one or two free ends.

One of the functions of the assembly turret 3 is to form the tampons into rosette shape by inverting the sacks to assume the condition illustrated in FIG. 3. As seen therein, the tampon structure has a generally cylindrical body defined by the exterior portion 4a and a generally conical re-entrant portion defined by the interior portion 4b, the structure in the condition illustrated being ready for radial compaction and insertion into a tube type inserter, which compacting and assembly operations are also performed on the assembly turret 3.

The completed and assembled tampon and inserter is illustrated in FIG. 4, the compacted, rosette shaped tampon, indicated at 4c, being contained within the upper portion of a tubular outer inserter part 8 having a nose 9 which is defined by a plurality of petals, two of which are indicated at 10 and 10a, which flex outwardly to permit discharge of the tampon from the inserter. At its trailing end 11, the outer inserter has a plurality of non-connected gripping elements 12 which may terminate inwardly in a stop shoulder 13 to engage the cylindrical wall surface of the inner inserter part 14 which is of tubular configuration, having a leading or nose end 15 defined by an annular shoulder 16 through which the withdrawal string 6 passes, the inner inserter terminating at its trailing end 17 in an annular flange 18. The inner inserter also may be provided with detents 19 which coact with the cylindrical wall surface of the outer inserter 8 and with its stop shoulder 13 to maintain the inner and outer inserter parts in assembled condition. In use, the inner inserter 14 acts as a plunger to discharge the tampon through the nose of the outer inserter.

Referring again to FIG. 1, a supply of inner inserters 14 is delivered to the assembly turret 3 through conduit means 20, such as an air-conveying system, from a source of supply (not shown). The inner inserters are sequentially fed by the rotary feeding means 21 to each of the operating heads or stations 22 on the assembly turret at which the inserting, compacting and assembling operations take place. Similarly, a supply of outer inserters 8 is fed through conduit means 23 to the rotary feeding means 24 which sequentially delivers an outer inserter to each of the heads 22 as the assembly turret rotates. Transfer of the tampon sacks from the transfer mechanism 2 to the assembly turret 3 takes place as the heads 22 come into tangential relation with the transfer mechanism, which mounts sets of jaws, indicated generally at 25, which position the withdrawal strings for engagement by a string grabber forming a part of each operating head 22.

As each of the operating heads 22 proceeds beyond the transfer mechanism 2, the inverting, compacting and assembly of the tampon structures and their inserters takes place, the assembled structures being removed from the assembly turret 3 by the rotary discharge means 26, whereupon the operating cycle of the machine is completed and the heads again pass the rotary feeding means 21 to commence another operating cycle.

The Transfer Mechanism

For a general understanding of the transfer mechanism 2, reference is made to FIG. 5 of the drawings which diagrammatically illustrates its operation, the transfer mechanism comprising a wheel assembly having an upper rotary disc 30 and a lower or underlying rotary disc 31 which is of smaller diameter, the upper disc 30 having an axis of rotation indicated by the shaft 32, whereas the axis of rotation of the lower disc, indicated by the shaft 33, is displaced laterally relative to the shaft 32, the arrangement being such that the peripheries of the upper and lower discs will be effectively in vertical alignment at their point of nearest approach to the mechanism 1 from which the tampon sacks are suspended, and will be spaced apart by the greatest distance at their point of nearest approach to the assembly turret 3.

Each of the sets of jaws 25 comprises an upper jaw 25a mounted on the periphery of the upper disc 30 and a coacting lower jaw 25b mounted on the periphery of lower disc 31. As possibly best seen in FIG. 6, as each set of jaws approaches the mechanism 1, the upper and lower jaws will be in vertical alignment and will be jointly opened as the withdrawal string 6 of a tampon sack suspended from the mechanism 1 is presented to the jaws, whereupon the jaws are closed in clamping engagement with the withdrawal string, the opening and closing movement of the jaws being effected by the action of cam means 34 having cam roller 35 in contact with a cam track 36. The speed of rotation of the transfer mechanism will be somewhat slower than the mechanism 1, and the upper and lower jaws will be positioned so that the withdrawal strings will overrun the open jaws and will be drawn into the jaws just prior to their closing.

The engagement between the upper jaw 25a and the withdrawal string 6 will be sufficiently loose to permit slippage of the string relative to the jaw, whereas the lower jaw is in tight clamping engagement with the withdrawal string. With this arrangement, as the discs rotate toward the assembly turret 3, the upper and lower jaws in each set will move apart and, in so moving, the withdrawal string 6 will be partially pulled through the looser top jaw so as to draw each string into essentially horizontal position as it approaches the assembly turret, such drawing apart of the strings being illustrated in FIG. 5.

Each withdrawal string is thus horizontally disposed as it is presented to an operating head 22 on the assembly turret, and the speed of rotation of the discs 30 and 31 relative to the assembly turret will be such that the string will overrun the station 22 and, in so doing, the string may be readily engaged by a string grabbing means 37 forming a part of each head 22, as possibly best seen in FIG. 7. Once the withdrawal string 6 has been engaged by the string grabbing means 37, the lower jaw 25b will be opened by the action of a cam track 38 positioned to engage the cam follower 35, thereby releasing the tampon sack from the lower disc 31. Since the withdrawal string is loosely engaged by the upper jaw 25a, the remainder of the string will be pulled from the upper jaw as the rotation of the parts continues, the withdrawal string now being firmly and tightly engaged by the string grabbing means 37.

The transfer mechanism also incorporates means for removing the tampon sacks from the transfer mechanism in the event transfer to the assembly machine cannot be accomplished. As seen in FIGS. 8 and 8A, a fluid cylinder or solenoid 39 is mounted beneath the lower disc 31, the cylinder in turn mounting an arm 40 carrying an upstanding reject button 41 movable from a lowermost or inoperative position to an elevated or operating position in which it extends into the path of travel of an advancing withdrawal string, thereby forming an obstruction which engages the string and causes its free end to be pulled from the upper clamping jaw 25a, which is outermost, the withdrawal string thus being held solely by the innermost lower clamping jaw 25b. As will be evident, upon being pulled from the upper clamping jaw 25a, the string will dangle and no longer will be horizontally disposed and hence no longer positioned to be engaged by the string grabbing means 37. Consequently, at the point where the lower jaw 25b is opened by the action of cam track 38, which occurs just after the string grabber means 37 would have engaged the string had it been in normal operating position, the release of the string by the lower gripping jaw results in the tampon being dropped into an underlying reject chute 42, to thereby collect the rejected tampon sacks.

With the foregoing general description of the transfer mechanism in mind, reference is now made to FIG. 9 for a more detailed description. The transfer mechanism is mounted on a supporting frame 43 having an extension 44 which mounts a hub 45 in which the shaft 33 for the lower disc 31 is rotatably journaled, the shaft being driven through gear belt pulley 46 and gear belt 47 which may be connected to a source of power, although preferably the transfer mechanism will be driven by the sealing and loop knotting mechanism 1, the drive belt 47 being operatively connected to the drive means (not shown) for the latter mechanism, suitable protective means, such as an overload clutch being provided to guard the transfer mechanism from damage in the event of jams. Alternatively, the transfer mechanism may be driven from the assembly turret 3 or by a separate synchronized motor.

The supporting frame 43 includes an upper portion 48 lying to one side of the discs 30 and 31 which mounts a lateral extension 49 having a hub 50 in which the upper drive shaft 32 is rotatably journaled, the shaft 32 being driven from shaft 33 by means of a Schmidt coupling 51 which, as will be understood by the worker in the art, comprises a linkage which carries torque from one parallel shaft to another.

As seen in FIG. 9, the arm 40 mounting reject pin 41 is in its lower or inoperative position, but upon energization of the fluid cylinder 39 will be displaced upwardly to engage the withdrawal strings of the sacks to be rejected. The reject chute 42 may be conveniently provided at its upper end with a funnel-like deflector, indicated at 52, positioned to receive the rejected tampons upon their release by the lower gripping jaws 25b and deflect them downwardly into the reject chute 42.

Referring next to FIG. 10 which illustrates the relationship of the gripping jaws and their component parts, the upper jaw 25a is pivotally connected by pivot pin 53 to the hub-forming portion 54 of mounting plate 55 by means of which the upper jaw is secured to the upper rotating disc 30, attachment bolts 56 being provided to secure the mounting plate to the rotatable disc, preferably through slot-like openings 57 in the rotary disc which permits adjustment of the position of the clamping jaw 25a relative to the center of the upper disc 30. The gripping jaw 25a has a depending shoulder or flange 58 which forms an abutment for moving the gripping jaw 25a from the closed position illustrated in FIG. 12 to the open position illustrated in FIG. 12A. The jaw 25a is normally biased to the closed position by spring 59 the opposite ends of which are received in pockets 60 and 61 formed in the mounting plate 55 and jaw 25a, respectively. A shallow recess 62 is provided on jaw 25a adjacent its free end, which terminates in a shoulder 63 coacting with the vertical edge 64 of the mounting plate 55 to clamp the withdrawal string in the recess 62 when the jaw is in the closed position. Since the upper gripping jaw 25a loosely grips the string, the clamping pressure exerted by spring 59 will be only sufficient to hold the string in the recess 62 between the jaw 25a and the vertical edge 64 of the support plate.

The lower gripping jaw 25b is an integral part of the cam means 34 referred to in connection with FIGS. 6 and 7, which cam means comprises a rearwardly projecting arm 65 (seen in FIGS. 10 and 11) having a lateral extension 66 which mounts the cam roller 35. The cam means 34, including the gripping jaw 25b, is pivotally connected to a mounting plate 67 by means of a pivot pin 68 projecting downwardly from an extending ear 69 forming part of mounting plate 67 into the underlying arm 65 of which the jaw 25b is an integral part. A spring 70 normally biases the clamping jaw 25b to the closed position, the spring being received at one end in a pocket 71 in the mounting plate 67 and at its opposite end in a pocket 72 in the clamping jaw. A guide pin 73 projects outwardly from the vertical edge 74 of the mounting plate 67, and is adapted to be received in a mating recess 75 in the lower jaws 25b. With this arrangement, the guide pin 73 lies in close proximity to the ear 69 and is of a length such that it effectively forms a stop for the string, i.e., when the jaw 25b is closed, the string is effectively clamped between the vertical edge 74 of the mounting plate 67 and the opposing surface of jaw 25a lying outwardly beyond guide pin 73.

In operation, when the cam roller 35, which is operatively connected to the lower jaw 25b, contacts cam track 36 to effect opening movement of the jaws, it will be evident that as the cam track 36 presses against the cam roller 35, the unitary assembly comprising the lower gripping jaw 25b, the rearwardly projecting arm 65 and lateral extension 66, will pivot about pivot pin 68, thereby pivoting the lower jaw to the open position illustrated in FIG. 11A. It will be noted that the lower jaw 25b has a projecting tip 76 which, as will be evident from FIG. 10, lies immediately inwardly of the depending shoulder 58 of upper jaw 25a. Thus, when the lower jaw 25b is moved from its closed to its open position, the projecting tip 76 will press against the depending flange 58 of upper jaw 25a and concurrently move the upper jaw to the open position. Of course, as soon as the cam roller 35 is released by its cam track, both jaws will be freed to return to their closed positions under the influence of their respective springs, thereby clamping the withdrawal string between them.

While a separate cam rail 38 at the opposite side of the transfer mechanism serves to reopen the lower clamping jaws 25b as the strings are engaged by the string grabbers on the assembly turret, such opening movement will have no effect on the upper gripping jaws since the upper jaws are spaced laterally from the lower jaws and hence out of position to be actuated by the lower jaws.

The mounting plates 67 for the lower jaws are provided with elongated slots 77 by means of which they are mounted on the rotary disc 31, as by means of mounting bolts 78. The slots 77 are relatively long so that the sets of gripping jaws just described may be utilized to handle strings of different lengths, which may be readily accomplished by changing the position of shaft 33 mounting the lower disc 31, the elongated slots in the lower mounting plates 67 permitting a wide latitude of adjustment to bring the lower jaws into vertical alignment with the upper jaws at the point where the strings are received from the mechanism 1.

Inserter Feeding Means

Reference is next made to FIG. 13 for a general description of the operation of the inserter feeder means. While the illustration is directed specifically to the feeder means for the outer inserters 8, it is to be understood that the feeding means for the inner and outer inserters are essentially identical in construction and operation except for specific differences hereinafter noted.

The conduit means 23 through which the outer inserters 8 are delivered terminates in a tubular discharge section 80 having a holder 81 at its far end, the holder having a screen 82 defining its remote end which will readily pass the air utilized to advance the inserters but will stop the nose of each inserter in proper position for engagement by a feeder wheel composed of inner disc 83 and outer disc 83a which, as the wheel rotates, engages each inserter and accelerate it sideways up to a surface speed and position matching an operating head on the assembly turret. The feeder wheel receives the inserters in a horizontal position and turns them through an angle of 90° by the action of the 45° drive shaft 84, the inserters being presented to the assembly turret in vertically disposed position, as indicated by the inserter 8a in FIG. 13.

In the case of the inner inserters 14, they will travel through the discharge section 80 in nose to tail relation, successively entering the holder 81 as the preceding inserter is engaged and moved sideways by the feeder wheel 83, such sideways movement releasing the next succeeding inserter for movement into the holder 81. However, in the case of the outer inserters 8, which have relatively fragile petals at their nose end, an escapement wheel 85 is provided in discharge section 80 to hold back a second inserter while the first is being moved sideways by the feeder wheel, since it is this sideways movement which causes damage to the petals of the outer inserters if they are in nose to tail relation. The lugs 86 on the escapement wheel 85 are preferably positioned to engage the gripping elements 12 on the trailing ends of the inserters. Both the inner and outer inserter feeding means are provided with retractable gates 87 controlled by a solenoid or fluid cylinder 88 to shut-off the supply of inserters to the feeding wheels as my be required during start-up or adjustment of the apparatus.

Referring next to FIG. 14 for a more defined description, the feeder means 21 for the inner inserters is mounted on a vertical support 89, and the feeding means 24 for the outer inserters is mounted on a vertical support 90, the supports 89 and 90 also serving as supports for an overhead platform 91 which mounts the prime mover 92 from which the various operating components are driven. A coupling 93 connects the prime mover to a gear reducer 94 to which a vertical line shaft 95 is connected to carry torque down to a right angle gear box 96 which drives the horizontal drive shaft 97. The drive shaft 97 is connected by drive belt 98 to the gear box 99 for the inner inserter feeding means 21, and the shaft is connected by drive belt 100 to the gear box 101 which drives the outer inserter feeding means 24.

Referring next to FIG. 17 which, while specifically illustrating the feeding means 24, is essentially identical in construction and operation to the feeding means 21, except for the differences previously noted. Thus, the gear box 101 drives the feeder wheel drive shaft 84 to thereby drive the inner and outer discs 83 and 83a which are fixed to the shaft for joint rotation therewith. As possibly best seen in FIG. 17, the inner and outer discs 83 and 83a have aligned sets of elongated slots 102 and 102a having trailing shoulders 103 and 103a which, as the discs pass through the holder 81, engage and move sideways an inserter positioned in the holder 81 with its nose against screen 82. As possibly best seen in FIG. 16, the holder 81 has a slotted far side wall 104 and a slotted bottom wall 105 through which the feeder wheel segments 83 and 83a pass, the rear or trailing side of the holder 81 being open except for a depending spring finger 106 which acts to press and align the inserters with respect to the trailing shoulders 103 and 103a as the inserters are moved sideways out of the holder. The inserters are held in the slots 102 and 102a by the curved hold-down rods 107 and 107a mounted on spaced apart brackets 108 which act to maintain the inserters in the slots 102 and 102a as the discs rotate, the hold-down rods maintaining the inserters in the slots until they have been uprighted, i.e., brought to a vertical position at their point of closest approach to the assembly turret. As the inserters approach the vertical position, they are engaged by stripping rods 109 and 109a mounted on bracket 109b, the stripping rods acting to discharge the inserters from the feeder wheel as the inserters pass beyond the terminal ends of hold-down rods 107 and 107a. As will become apparent hereinafter, as the inserters are stripped from the feeder, the stripping rods 109 and 109a will press them into holders forming a part of each head on the assembly turret.

While the inserters will be delivered to the discharge section 80 by means of air under pressure which carries the inserters through their respective feed conduits, it is preferred to provide additional air jets to accelerate the movement of the inserters into the holder 81. To this end, and as illustrated in FIG. 18, slots 110 and 110a are formed in the opposite sides of the discharge section 80 into which air jets 111 and 111a project, the air jets facing in the direction of the holder 81 and serving to accelerate the inserters as they move toward their respective holders. In the case of the feeder means 24 for the outer inserters, which includes the escapement wheel 85, the air jets are positioned to impinge upon the inserters as they are released by the escapement lugs 86.

Air under pressure may be supplied to the jets 111 and 111a through a common feed tube 112.

As shown in FIGS. 14 and 17, the escapement wheel 85 for the feeder means 24 may be driven by a drive shaft 113, the opposite end of which is connected through drive belt 114 to a shaft 115 driven by drive belt 100, the shaft 115 mounting pulley wheel 116 which is engaged by drive belt 100, the shaft 115 thus driving both the gear box 101 and the escapement wheel 85.

Inverting, Compacting, And Assembling

Reference is next made to FIG. 19 and its continuation, which diagrammatically illustrates the various operations performed by each of the operating heads or stations 22 during each revolution of the assembly turret 3, the various positions of the components being sequentially indicated by the reference letters A through J.

As seen at position A, which is the position of the parts at the start of an operating cycle, the principal components of each head comprise an inversion chamber 120 having a vertically reciprocating inversion tube 121. Mounted beneath and in axial alignment with the inversion chamber 120 and inversion tube 121 is a compression cone 122 which mounts a holder 123 for the outer inserters 8. A compression chamber 124 having opposing jaws 124a and 124b lies immediately beneath and in axial alignment with the compression cone 122. A holder 125 for the inner inserters 14 underlies the compression chamber 124, with a reciprocating assembly tube 126 underlying the holder 125, and the previously described string grabbing means 37, which comprises a reciprocating rod assembly, projects upwardly within the assembly tube 126.

As the head reaches position B, it is presented to the inner inserter feeding means 21 which feeds an inner inserter 14 into the holder 125, with the lowermost flanged end 18 of the inner inserter seated on the upper end of assembly tube 126 and with its upper end lying within the confines of jasws 124a and 124b. Immediately upon the positioning of the inner inserter in the holder 125, the string grabbing means 37 commences upward movement through the inner inserter and into the compression chamber 124, the jaws 124a and 124b of the compression chamber concurrently moving from the open to the closed position, the parts thereby assuming the condition illustrated at position C in which the outer inserter feeding means 24 displaces an outer inserter 8 laterally into holder 123. As will be evident from position C', which is the same as but taken at right angles to position C, the holder 123 is mounted on the outer side of compression cone 122 and hence the outer inserter 8 is held in laterally displaced position with respect to the common vertical axis of the other components. As the outer inserter is placed in its holder, the string grabbing rod 37 continues its upward movement through compression cone 122, the parts thereby assuming the condition illustrated at position D as the head 22 comes into tangential relation to the transfer mechanism 2 where the string grabbing means 37 engages the withdrawal string 6 of the tampon sack 4 upon being presented to the head 22 in the manner previously described.

As the head 22 moves beyond the transfer mechanism 2, the inversion process begins with the string grabbing means 37 moving downwardly, thereby pulling the tampon sack into the compression cone 122 by a distance sufficient to position the sack vertically, as illustrated by position E, at which position the inversion chamber 120 and inversion tube 121 have moved downwardly in preparation for inversion, such downward movement being accompanied by the drawing of vacuum on inversion tube 121, the inversion tube engaging the uppermost end of the sack and holding it against the end of the tube by vacuum. When the inversion chamber 120 has completed its downward movement to position F, the inversion tube will have moved upwardly to the position shown at F, whereupon vacuum is preferably discontinued to the inversion tube and vacuum is drawn on inversion chamber 120 to draw the tampon sack upwardly into the inversion chamber and, in so doing, the sack is formed into rosette shape as it is inverted about the inversion tube 121. At the same time, the string grabbing rod 37 moves upwardly to insure that the inversion of the sack is uniform, i.e., insure that the sack is centered on the inversion tube during the inversion operation, and to this end the string will be maintained sufficiently taut to prevent the sack from tilting to one side of the inversion tube as it is drawn into the inversion chamber.

Once the sack is fully inverted, vacuum to the inversion chamber 120 is discontinued, the inversion tube 121 begins to move downwardly, and air under pressure is introduced into the inversion tube to propel the sack downwardly into the underlying compression cone 122, as seen at position G. Concurrently, the string grabbing means 37 is moved downwardly and, as the downward movement of the string grabbing means continues, the inverted tampon sack is pulled by its string through the funnel-shaped compression cone and into the underlying cylindrical compression chamber 124, the parts thereby assuming the condition illustrated at position H, in which position the tampon sack has been compacted to final size within the compression chamber 124 and the withdrawal string lies within the confines of the inner inserter, where it is released by the string grabbing means 37.

As illustrated at H', which is the same as but taken at right angles to position H, when the tampon sack is completely within compression chamber 124, the compression cone 122 is shifted laterally to bring the outer inserter 8 into vertical alignment with the compressed tampon in the compression chamber and the underlying inner inserter 14, whereupon, as illustrated at position I, the inversion tube 121 moves downwardly and presses against the upper end of holder 123, which is slidable relative to the compression cone 122, and the outer inserter 8 is firmly seated on the upper surface of the compression chamber by the action of holder 123 against the gripping elements 12 of the outer inserter, whereupon the assembly tube 126 moves upwardly, thereby forcing the inner inserter 14 through the compression chamber 124 and, in turn, forcing the compressed tampon and the inner inserter into the outer inserter, thereby completing the assembly operation. The parts then move to position J, the inversion chamber 120 and the inversion tube 121 moving upwardly; the assembly tube 126 and the enclosed gripping rod 37 moving downwardly; the jaws 124a and 124b of the compression chamber opening; and the compression cone shifted radially outwardly to overlie the now-open jaws of the compression chamber, the assembled tampon structure thus being removed from between the open jaws of the compression chamber 124 and held solely by the holder 123. It is in this position that the assembled tampon structure is removed from the holder 123 by means of a stripper bar 127, which transfers the finished product to the discharge means 26 which conveys the finished product away from the turret.

The Assembly Turret

Referring next to FIG. 20, which illustrates details of the assembly turret, the turret comprises a fixed base 130 to which an internal support structure 131 is fixedly secured, the support structure mounting at its upper end a centrally disposed vertical shaft 132 on which drive wheel assembly 133 is rotatably mounted by bearing means 134, the drive wheel being engaged by a timing belt 135 which, as will be evident from FIGS. 14 and 15, is operatively connected to and driven from line shaft 95 which is connected to gear reducer 94 powered by prime mover 92. Each of the operating heads 22 is secured at its upper end to a disc 136 forming a part of the drive wheel assembly 133 by means of an attachment bracket 137; and at its bottom end each of the heads is attached to a disc assembly 138 by means of lower attachment brackets 139. The lower disc assembly 138 is rotatably journaled relative to fixed base 130 by bearing means 140 comprising a shielded ball bearing assembly which supports the weight of the rotating portion of the turret.

The centrally disposed support structure 131 mounts the cam tracks which control the operation of the various components of each head and also mounts the ports and conduits which draw vacuum on inversion chamber 120 and inversion tube 121, as well as supplying air under pressure to the inversion tube during ejection of the tampons from the inversion chamber. Thus, the cam track 141 controls the reciprocating movement of inversion tube 121, and the cam track 142 controls the movement of inversion chamber 120. Lateral shifting movement of compression cone 122 is controlled by cam track 143, whereas opening and closing movement of compression chamber 124 is controlled by cam track 144. Cam track 145 controls reciprocating movement of assembly tube 126, and cam track 146 reciprocates string grabbing means 37, the cam track 147 also operating a component of the string grabbing means in a manner which will be explained hereinafter. As will be evident, all of the cam tracks are internal with respect to the heads 22, the heads revolving around the cam tracks, which arrangement allows for easy removal of the heads for repair or replacement and additionally provides good machine visibility. In a preferred embodiment of the invention, 45 heads are mounted on the turret, thereby forming 45 complete tampon structures during each revolution of the turret.

The support structure 131 also mounts the vacuum conduit means 148 for drawing vacuum on the inversion chamber 120, and also vacuum-pressure conduit means 149 for selectively drawing vacuum on, or supplying air under pressure to, inversion tube 121.

The Operating Heads

The various operating components of each head 22 are mounted on a spaced apart pair of vertically disposed support rods 150 extending between the upper attachment brackets 137 and lower attachment brackets 139. Thus, the entire head may be removed from the truret by simply unscrewing the bolts by means of which the attachment brackets are secured to the upper and lower disc assemblies 136 and 138, together with bracket 196 bolted to intermediate rotary support plate 197.

The support rods 150 also serve as the means for mounting the various parts of each head for vertical movement. Thus, as also seen in FIG. 20, the inversion tubes 121 are mounted on mounting blocks 152 which are slidable along the rods 150, their movement being controlled by the cam rollers 153 which engage in recessed or closed cam track 141 and hence are positively moved upwardly and downwardly in accordance with the configuration of the cam track. Similarly, the mounting blocks 154 for the inversion chambers 120 slide along the rods 150 as the cam rollers 155 follow the closed cam track 142. The mounting blocks 156 for the compression cones 122 and compression chambers 124 are fixedly secured to the support rods 150 since these components do not move vertically, whereas the assembly tubes 126 are mounted on slidable mounting blocks 157 having cam rollers 158 engaged in closed cam track 145. The string grabbing rod assemblies 37 are mounted on slidable blocks 159 having cam rollers 160 which engage in closed cam track 146.

Compression Cone And Compression Chamber

FIG. 21 illustrates details of the compression cone 122 and compression chamber 124. The compression cone 122, which preferably is formed from clear plastic, has a frusto-conical inner surface 161 which, as previously explained, serves as a seat for positioning the tampon sack for inversion, and also serves to compact the inverted sack to final size as the sack is drawn downwardly through the cone into the underlying compression chamber. The cone is mounted on horizontally disposed rods 162 and 163 which are slidably journaled in mounting block 156 fixedly secured to support rods 150, the rearmost ends of the rods 162 and 163 being secured to a block 164 mounting cam roller 165 which engages upwardly facing closed cam track 143 mounted on central support structure 131. When the cam roller 165 is in the position illustrated, the compression cone will overlie and be in axial alignment with the compression chamber 124, and the holder 123 carrying the outer inserter 8 is displaced laterally with respect to the compression chamber. As seen in FIG. 24, when the cam roller 165 is moved to the opposite reach of the cam track, indicated at 143a, the block 164 will move rods 162 and 163 from left to right, thereby displacing the compression cone 122 inwardly and bringing outer inserter 8 into vertical alignment with the underlying compression chamber 124. This movement takes place as the parts move to position H—H' illustrated in FIG. 19. The compression cone is returned to its outermost position overlying the compression chamber 124 when the parts reach position J.

The holder 123 for the outer inserter is also preferably formed from plastic and has integral resilient jaws 123a and 123b at both top and bottom which enter into clamping engagement with the outer inserter as the inserter is displaced laterally into the jaws by the outer inserter feeder 24, the configuration of the jaws being seen in FIG. 23. The holder 123 has a base 166 slidably received in dovetail slot 166a in compression cone 122, the base being biased upwardly into contact with shoulder 167 by spring 168. The holder 123 is adapted to be displaced downwardly by the action of the inversion tube 121 when the parts assume position I illustrated in FIG. 19, the lowermost edge of the inversion tube 121 pressing against the flat upper surface 169 of the holder. As will be evident, when the holder is released by the inversion tube 126, it will be returned to its uppermost position by the action of spring 168.

As also illustrated in FIGS. 21 and 24, the mounting block 156 terminates downwardly in a yoke 170 to which an arm 171 is pivotally connected by pivot pin 172, the arm mounting cam roller 173 at its innermost end which engages previously identified cam track 144 mounted on support structure 131. The arm 171 is normally biased to the position illustrated in FIG. 21 by means of depending pin 174 which extend downwardly through slot 175 in the arm 171, the upper end of the pin being received in a downwardly opening recess 176 in mounting block 156 where it is attached to the block by pivot pin 177. The arm 171 is biased upwardly by spring 178 surrounding the lower end of pin 174 and extending between washer 179 seated against the undersurface of arm 171 and a collar 180 at the distal end of the pin. As possibly best seen in FIG. 22, the arm 171 has an opposing pair of downwardly and outwardly inclined cam surfaces 181 and 182 adapted to contact cam followers 183 and 184 connected, respectively, to the arms 185 and 186 of previously identified jaws 124a and 124b defining the opposite sides of compression chamber 124. The jaws 124a and 124b are pivotally connected to a common hinge pin 187 passing through common knuckle 188 (FIGS. 21 and 24) forming a part of mounting block 156, the jaw 124a having knuckles 189 and 190, and the jaw 124b having knuckles 191 and 192.

When the arm 171 is in the position illustrated in FIGS. 21 and 22, the jaws 124a and 124b will be in the closed position, being maintained in the closed position by the cam tracks 181 and 182 which bear against the cam followers 183 and 184, respectively. When the arm is rocked in a counterclockwise direction (as viewed in FIGS. 21 and 24) about its pivot pin 172, the cam surfaces 181 and 182 will be moved downwardly, thereby effectively permitting the cam rollers 183 and 184 to move upwardly along the inwardly inclined cam surfaces 181 and 182, and the jaws 124a and 124b will open to the position illustrated in FIGS. 24 and 25 under the influence of spring 193 extending between the inner surfaces of the jaws adjacent the hinge pin 187. This action will take place when the cam follower 173 contacts a rise in cam track 144; conversely, when the cam follower 173 drops off the rise, a coacting cam track 144a will urge the arm 171 upwardly, thereby camming the rollers 183 and 184 outwardly to close the jaws against the compression of spring 193, the jaws being retained in the closed position by the action of spring 174.

Preferably, the inner surfaces of jaws 124a and 124b will be lined throughout their upper portions with plastic inserters 194, and in their lower portions with a resilient, sponge-like plastic material 195 to accommodate the flange 18 on the bottom of the inner inserter since, of necessity, the compression chamber is longer than the inner inserter and hence the lowermost end of the inner inserter will be shoved into the compression chamber as an incident of its engagement with the overlying outer inserter, as will be evident from FIG. 24. In their sequence of operation, the jaws 124a and 124b will be opened as the head reaches position J, as illustrated in FIG. 19, and will be closed as the parts move from position B to position C.

As also illustrated in FIG. 21, the inner insert holder 125, which is semi-cylindrical in configuration and faces outwardly toward the feeding means 21, is mounted on a bracket 196 fixedly secured to support rods 150 and also bolted along with the support rods to an intermediate support plate 197 which rotates about the central support structure 131. The bracket 196 also serves as a means to slidably journal the upper portion of assembly tube 126, the upper end of which has an enlarged flange 198 on which the lowermost flanged end 18 of the inner inserter 14 seats when received by holder 125.

Assembly Tube And String Grabbing Means

As seen in FIG. 26, which illustrates details of the assembly tube 126 and string grabbing means 37, the lowermost end of assembly tube 126 is fixedly secured to an extension 199 forming a part of mounting block 157 which is slidable along rods 150 under the influence of cam roller 158 and closed cam track 145.

As also seen in FIG. 26, string grabbing means 37 comprises a tubular outer grabber rod 200 movable axially through the assembly tube 126, together with an inner grabber rod 201 extending through and axially movable relative to the outer grabber rod 200. The outer grabber rod 200 has a slot 202 adjacent its upper end which exposes the upper end of the inner grabber rod 201, the slot 202 being positioned to be engaged by the withdrawal string of a tampon sack as the sack is transferred to the assembly turret. At the time of transfer, the inner grabber rod 201 will be moved downwardly relative to the outer rod 200 to the position illustrated in FIG. 26A, and upon the withdrawal string 6 being received in the slot 202, the inner grabber rod 201 will snap closed and its inclined upper surface 203 will engage the string 6 and clamp it between the inclined surface 203 of inner grabber rod 201 and the mating inclined surface 204 of outer grabber rod 200.

Axial movement of the inner grabber rod 201 is effected by means of cam arm 205 pivotally connected by pivot pin 206 to fitting 207, the arm 205 terminating rearwardly in a cam roller 208 positioned to contact cam rail 209. The forward end of arm 205 is bifurcated, having a pair of forwardly projecting fingers 210 lying on opposite sides of the fitting 207, the fingers being positioned to contact a crossbar 211 which projects outwardly from the opposite sides of fitting 207 through an elongated slot 212, the crossbar being movable axially in the slot 212 under the influence of the fingers 210 of cam arm 205. The inner grabber rod 201 extends downwardly through the crossbar 211 where it is engaged by a collar 213, the lowermost end of the rod being surrounded by a spring 214 extending between the collar 213 and the sock-like fitting 215 in which the opposite end of the spring is received.

With the arrangement just described, when the arm 205 is pivoted in a counterclockwise direction about its pivot pin 206, the fingers 210 will press downwardly on the crossbar 211 which bears against the collar 213 and hence urges the rod 201 downwardly against the compression of spring 214, the socket-like fitting 215 being of a depth to permit the lowermost end of rod 201 to move downwardly within the fitting. This action causes the upper end of the inner grabber rod to move from the closed position shown in FIG. 26 to the open position shown in FIG. 26A. The configuration of the cam rail 209 is such that the cam arm 205 will be rocked to depress the inner grabber rod just prior to the engagement of the grabber rod assembly with the string of a tampon to be transferred to the assembly turret, and the cam arm 205 will be released when the string is in the position shown in FIG. 26A, whereupon the inner grabber rod 201 will be thrust upwardly under the influence of spring 214.

The entire grabber rod assembly 27 is raised and lowered by means of mounting block 159 slidable along the support rods 150 under the influence of cam roller 160 riding in closed cam track 146 which sequentially raises and lowers the grabber rod assembly to the various operating positions previously described.

Mechanism is also provided to protect the grabber rod assembly should a jam or other obstruction prevent the outer grabber rod 200 from moving upwardly to its extended position. To this end, the lower portion of outer grabber rod 200 is slidably journaled in an extension 216 of mounting block 159, the lowermost end of the outer grabber rod being fixedly secured to the fitting 207 which underlies the extension 216. The outer grabber rod 200 is biased upwardly by means of spring 217 which surrounds the outer grabber rod, the spring extending between the extension 216 and a collar 218 fixedly secured to the outer grabber rod. It will be evident, however, that the outer grabber rod may be deflected downwardly relative to the extension 216 against the compression of spring 217; when deflected downwardly, the outer grabber rod 200 will carry with it fitting 207 to which it is fixedly secured.

The extension 216 has an annular bore 216a in which a plunger 219 is slidably received, the plunger having a rearwardly extending portion 220 of reduced diameter which mounts cam roller 160, the reduced diameter portion of the plunger being surrounded by a spring 221 which normally biases the plunger 219 outwardly. The plunger has a vertically disposed elongated slot 222 through which the outer grabber rod 200 freely passes, the slot terminating at its inner end in a shoulder 223 which is engaged by a tongue 224 forming a part of fitting 207, the tongue projecting upwardly through an opening 225 in extension 216 in communication with the annular bore 216a.

With the arrangement just described, if the outer grabber rod 200 strikes an obstruction as it is being moved upwardly under the influence of cam track 146, the obstruction will deflect the grabber rod downwardly against the compression of spring 217, and such downward movement will carry with it fitting 207, thereby moving tongue 224 downwardly and releasing it from contact with shoulder 223 of plunger 219, whereupon the plunger is shifted axially outwardly under the influence of spring 221. Such movement will pull cam roller 160 out of cam track 146, and the entire assembly mounted on block 159 is thereby freed to drop to its lowermost position. As will be evident from FIG. 26B, the axial shifting of plunger 219 results in tongue 224 contacting the undersurface of plunger 219 in the area 219a. The grabber rod assembly may be reset by displacing the plunger 219 inwardly against the compression of spring 221, such movement freeing the tongue 224 for upward movement under the influence of spring 217 upon passage of the shoulder 223 beyond the vertical edge 224a of the tongue 224, the parts thereby reassuming the position illustrated in FIG. 26. Such reset movement projects the cam roller 160 inwardly for reengagement with the cam track 146.

The plunger 219 may be automatically reset by a reset shoe diagrammatically indicated at 226 in FIGS. 20 and 26, located to swing into position whenever it is contacted by the extended plunger 219 of an overloaded grabber rod assembly which has dropped to its lowermost position, the shoe serving to reset the plunger 219 by ramping the cam follower 160 back into the cam track 146. Preferably, the reset shoe will be positioned to reset the plungers at the end of the operating cycle, i.e., at a point intermediate the discharge means 26 and inner inserter feeding means 21.

Inversion Chamber And Inversion Tube

Referring next to FIG. 27 for details of the inversion chamber and reciprocating inversion tube, the tube 121 is slidably journaled at its upper end in an integral extension 227 of mounting block 152 which carries cam roller 153 engaged in closed cam track 141, the configuration of the cam track serving to raise and lower the inversion tube. The upper end of the inversion tube 121 is closed by a plug 228, and a guide bar 229 projects outwardly from the top of the tube and then downwardly along the outermost side edge of the extension 227. An upper collar 230 is fixedly secured to the inversion tube 121 adjacent its upper end and normally seats against the upper surface of extension 227, the tube being surrounded by a spring 231 extending between the undersurface of extension 227 and a lower collar 232 also fixedly secured to the inversion tube. This arrangement permits limited shock absorbing movement of the inversion tube relative to the extension 227 when the inversion tube is moved downwardly into contact with the outer inserter holder 123 to urge the holder downwardly to seat the outer inserter on the underlying compression chamber, which takes place at position I illustrated in FIG. 19.

A pressure-vacuum passage 233 extends through the extension 227 from port 234 in the inversion tube 121 to a face plate 235, preferably formed from plastic, mounted on the innermost end of block 152. The face plate 235 is positioned to lie in close, but preferably non-contacting, relation to the opposing face plate 236 forming a part of pressure-vacuum conduit means 149. The face plate 235 has a port 237 positioned to communicate with slot-like ports in face plate 236. As diagrammatically illustrated in FIG. 27A, the face plate 236 is provided with an elongated port 238a which will be connected through conduit means 149 to a source of vacuum (not shown) to draw vacuum on the inversion tube 121 during the inversion of the tampon sacks, which takes place at position F shown in FIG. 19. Thereafter, the port 237 will come into communication with the slot-like port 238b which will be connected through the conduit means 149 to a source of air under pressure (not shown), thereby providing an air blast through the inversion tube 121 to blow the inverted tampon sack downwardly into the underlying compression cone 122.

As also illustrated in FIG. 27, the inversion chamber 120, which may be formed from transparent plastic if desired, has an inner annular chamber 239 separated from a concentric outer annular chamber 240 by a sleeve 241. The outer chamber is closed at its lower end but communicates at its upper end through ports 242 with an overlying chamber 243 comprising an extension of inversion chamber mounting block 156 which has an enlarged passage 244 communicating at one end with the chamber 243 and at its opposite end with a port 245 in face plate 246. The face plate 246 will lie in close proximity to the opposing face plate 247 of vacuum conduit means 148 which will draw vacuum on the chambers through an elongated slot-like port 248.

The sleeve 241 which separates inner chamber 239 from outer chamber 240 is provided with perforations 249, preferably equally spaced about its periphery in at least the lower portion of chamber 239. Such arrangement provides for the uniform drawing of vacuum on inner chamber 239 in which the inversion operation takes place, the outer annular chamber 240 insuring uniform air flow from the inner to the outer chamber through perforations 249, and the upper chamber 243 and its ports 242 insuring uniform air flow from the outer annular chamber to the upper chamber from which the air is exhausted through passage 244 and vacuum conduit means 148.

The inversion tube 121 projects downwardly through the centers of upper chamber 243 and underlying inner chamber 239, gaskets 250 and 251 providing an air-tight connection between the chambers and the inversion tube yet permitting relative axial movement between the inversion tube and chambers either under the influence of cam track 141 and cam follower 153 which raise and lower the inversion tube, or under the influence of cam track 142 and cam roller 155 which act to raise and lower the chambers.

In operation, the inversion chamber arrangement just described, coacting with the inversion tube, acts to draw the tampon sack into chamber 239 and invert it about the inversion rod 121, such operation being illustrated at position F in FIG. 19. The vacuum drawn on chamber 239, in addition to drawing the tampon sack upwardly into the chamber, also acts, through the uniformly spaced perforations 249 in the sleeve 241, to expand the tampon sack radially outwardly so as to bring its tubular wall surface into contact with the inner surface of sleeve 241, thereby assisting in centering the sack on the inversion tube to insure that it is not slanted to one side. In addition to radially expanding the tubular sack to conform to the cylindrical wall surface of sleeve 241, the vacuum perforations 249, acting through the porous material from which the sack is formed, also draw the enclosed aggregate (seen at 5 in FIG. 2) radially outwardly into contact with the expanded wall surfaces of the sack, thereby forming the aggregate into an essentially annular core which insures substantially uniform distribution of the aggregate throughout the periphery of the inverted tampon. This action lessens the density of the aggregate at the center of the core and effectively promotes the formation of an inverted sack in which the aggregate is uniformly distributed between the exterior and re-entrant portions of the inverted structure, indicated at 4a and 4b, respectively, in FIG. 3.

Product Discharge Means

Details of the assembled product discharge means 26, which comprises a transfer wheel, are illustrated in FIG. 28, the wheel 252 being mounted on a shaft 253 driven through gear box 254 from a line shaft 255. As seen in FIG. 14, the line shaft 255 extends upwardly on the far side of vertical support 89 where it is driven by drive belt 256 which, in turn, is driven from shaft 257 having a pulley wheel 258 driven by drive belt 135 which also drives the assembly turret, as possibly best seen in FIG. 15. The delivery wheel 252 is thus driven in timed relation to the rotation of the assembly turret.

Referring again to FIG. 28, the transfer wheel 252 is mounted at an inclined angle, preferably 45°, and carries a series of holders 258 extending at equally spaced apart intervals at its periphery, the holders being positioned to extend vertically when at the top of the path of rotation of the wheel, which is its point of closest approach to the assembly turret, the holders being horizontally disposed at the lowermost point in the path of travel of the transfer wheel. Each of the holders 258 has an upper jaw 258a and a lower jaw 258b, preferably formed of resilient material and of substantially the same configuration as the jaws 123a and 123b of the outer inserter holders 123 mounted on the compression cones 122 which, it will be recalled, move outwardly after the tampon structure has been fully assembled and the jaws of the underlying compression chamber have opened, as illustrated at position J in FIG. 19. It is at this point that the assembled tampon structure comes into contact with the stripper bar 127 which is positioned to enter between the assembled tampon structure and compression cone 122, thereby displacing the tampon structure laterally from the holder.

As will be apparent from FIG. 29, as each discharge holder 258 comes into alignment with holder 123 the stripper bar 127 will displace the tampon structure from the holder 123 and force it into the transfer holder 258. As the transfer wheel rotates, the tampon structure will be turned through 90° to an essentially horizontal position, at which point a stripper bar 259 will enter between the jaws of the transfer holder and remove the assembled tampon, which will be freed to drop into an underlying collection bin or onto a conveyor belt for delivery to a succeeding operation station for inspection and packaging.

As should now be apparent, the present invention provides integrated apparatus and procedures for forming tampons and assembling them in inserters in a continuous high speed operation. In its apparatus aspects, the invention contemplates the various components by means of which the tampon sacks are delivered to the assembly turret, manipulated on the assembly turret to form the sacks into rosette shape and thereafter compact and assemble them with their inserters, followed by the discharge of the completed product for subsequent processing; and in its method aspects, the invention contemplates the techniques and procedures by means of which the tampon sacks are manipulated to shape and assemble them with their inserters.

Numerous modifications of the invention have already been set forth, and additional modifications and variations will undoubtedly occur to the worker in the art upon reading this specification, and it is therefor not intended that the scope of the invention be limited other than in the manner set forth in the claims which follow.

The embodiments of the invention in which an exclusive property or privilege is claimed are defined as follows:

1. A method for forming and assembling tampons in inserters, comprising the steps of providing a tampon sack having an elongated tubular body containing a particulate material and a withdrawal string at one end, engaging and pulling on the withdrawal string to bring the tampon sack into vertical position with its withdrawal string lowermost, expanding the tubular body of the sack radially outwardly while maintaining the sack in vertical position by means of its withdrawal string, and as an incident of the radial expansion of the sacks folding the end of the sack opposite the withdrawal string inwardly along its longitudinal axis to form an exterior portion and a re-entrant inner portion, utilizing the withdrawal string to move the folded sack into a compression zone, compressing the folded structure radially inwardly to compacted cylindrical shape, positioning a tubular inserter in axial alignment with the compacted tampon, and displacing the tampon axially into the inserter.

2. The method claimed in claim 1 wherein the inserter comprises an outer part and an inner part, wherein the outer part is positioned in axial alignment with the compacted tampon at the upper end thereof, including the steps of positioning the inner insert part in axial alignment with the tampon at the lower end thereof, and displacing the inner part axially in the direction of the tampon to thereby insert the tampon into the outer part.

3. The method claimed in claim 2 including the step of inserting the upper end of the inner part into the lower end of the outer part as an incident of inserting the tampon into the outer part.

4. The method claimed in claim 1 including the steps of providing a cylindrical chamber having a diameter substantially equal to the diameter of the tubular body of the sack when in radially expanded condition, drawing the sack into the chamber and effecting radial expansion of its tubular body while contained within the chamber.

5. The method claimed in claim 4 including the steps of drawing a vacuum on said chamber, and utilizing the vacuum to draw the tampon sack into the chamber and to expand its tubular body radially outwardly.

6. The method claimed in claim 5 including the steps of providing an inversion tube axially movable within the chamber along its longitudinal axis, and effecting the folding of the sack by holding its uppermost end in contact with the end of the inversion tube, and drawing the tubular body of the sack upwardly around the inversion tube as an incident of the radial expansion of the tubular body of the sack.

7. The method claimed in claim 6 including the step of drawing a vacuum on the inversion tube to thereby hold the end of the sack in contact with the tube.

8. The method claimed in claim 7 including the steps of terminating the vacuum drawn on the chamber and the inversion tube when the folding of the sack is completed, and thereafter expelling the folded sack from the chamber by means of said inversion tube.

9. The method claimed in claim 8 including the step of introducing air under pressure into the inversion tube to assist in expelling the folded sack from the chamber.

10. The method claimed in claim 9 including the step of positioning a funnel-shaped compression member beneath the inversion chamber with its smaller end lowermost, positioning a cylindrical compression chamber immediately beneath said funnel-like compression member, and pulling the folded sack through said funnel-like member and into the compression chamber by means of its withdrawal string 11. The method claimed in claim 10 wherein said inserter comprises an outer part and an inner part, including the steps of positioning the inner inserter part in axial alignment with the lower end of said compression chamber, displacing said funnel-shape-shaped compression member relative to said compression chamber and positioning said outer inserter part in axial alignment with the upper end of said compression chamber, displacing said inner inserter part axially through said compression chamber to thereby insert the compressed sack into the outer inserter part, including the step of pulling the withdrawal string into the inner inserter part as an incident of pulling the compressed sack into the compression chamber.

* * * * *

UNITED STATES PATENT OFFICE
CERTIFICATE OF CORRECTION

PATENT NO. : 4,067,087
DATED : January 10, 1978
INVENTOR(S) : John George Mast, Jr.

It is certified that error appears in the above-identified patent and that said Letters Patent are hereby corrected as shown below:

Column 3, line 65, "heads of stations" should read --heads or stations--.

Column 18, line 50, "sock-like" should read --socket-like--.

Signed and Sealed this

Fourth Day of July 1978

[SEAL]

Attest:

RUTH C. MASON
Attesting Officer

DONALD W. BANNER
Commissioner of Patents and Trademarks